US012576362B2

(12) United States Patent
Hashimoto et al.

(10) Patent No.: US 12,576,362 B2
(45) Date of Patent: Mar. 17, 2026

(54) METHOD FOR CONCENTRATING RAW MATERIAL SOLUTION, AND SYSTEM FOR CONCENTRATING RAW MATERIAL SOLUTION

(71) Applicant: Asahi Kasei Kabushiki Kaisha, Tokyo (JP)

(72) Inventors: Tomotaka Hashimoto, Tokyo (JP); Yuki Suga, Tokyo (JP); Masato Mikawa, Tokyo (JP); Ryoichi Takada, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 918 days.

(21) Appl. No.: 17/641,207

(22) PCT Filed: Sep. 17, 2020

(86) PCT No.: PCT/JP2020/035322
§ 371 (c)(1),
(2) Date: Mar. 8, 2022

(87) PCT Pub. No.: WO2021/054406
PCT Pub. Date: Mar. 25, 2021

(65) Prior Publication Data
US 2024/0050897 A1　　Feb. 15, 2024

(30) Foreign Application Priority Data
Sep. 17, 2019　　(JP) ................................. 2019-168623

(51) Int. Cl.
*B01D 61/00* (2006.01)
*B01D 61/36* (2006.01)
(Continued)

(52) U.S. Cl.
CPC ..... *B01D 61/0024* (2022.08); *B01D 61/3641* (2022.08); *B01D 61/58* (2013.01);
(Continued)

(58) Field of Classification Search
CPC . B01D 61/002; B01D 61/36; B01D 2317/022
See application file for complete search history.

(56) References Cited

U.S. PATENT DOCUMENTS 8,029,671 B2　10/2011　Cath et al.
9,248,405 B2　2/2016　McGinnis et al.
(Continued)

FOREIGN PATENT DOCUMENTS

CN　　103073146 A　　5/2013
CN　　108993146 A　　12/2018
(Continued)

OTHER PUBLICATIONS

Campos, Juacyara Carbonelli, et al. "Oilfield wastewater treatment by combined microfiltration and biological processes." Water Research 36.1 (2002): 95-104. (Year: 2002).*
(Continued)

*Primary Examiner* — Bradley R Spies
(74) *Attorney, Agent, or Firm* — Morgan, Lewis & Bockius LLP

(57) ABSTRACT
Provided are a concentration method and system for concentrating a raw material solution, and in which a raw material solution containing a solute and a solvent is concentrated to obtain a concentrate of the raw material solution, wherein the solvent contains water and an organic solvent. In the method and system for concentrating a raw material solution, the system includes a combination of: a first concentrating means for removing water in the raw material solution by means of a forward osmosis method; and a second concentrating means for evaporating and
(Continued)

removing water and an organic solvent in the raw material solution.

12 Claims, 8 Drawing Sheets

(51) Int. Cl.

| | | |
|---|---|---|
| *B01D 61/58* | (2006.01) | |
| *C07C 29/86* | (2006.01) | |
| *C07C 253/34* | (2006.01) | |
| *C07D 209/20* | (2006.01) | |
| *C07K 1/14* | (2006.01) | |

(52) U.S. Cl.
CPC ............ *C07C 29/86* (2013.01); *C07C 253/34* (2013.01); *C07D 209/20* (2013.01); *C07K 1/145* (2013.01); *B01D 61/0022* (2022.08); *B01D 61/366* (2013.01); *B01D 2317/022* (2013.01); *B01D 2317/08* (2013.01)

(56) References Cited

U.S. PATENT DOCUMENTS

| | | | |
|---|---|---|---|
| 2006/0144789 | A1 | 7/2006 | Cath et al. |
| 2011/0203994 | A1 | 8/2011 | McGinnis et al. |
| 2012/0267307 | A1 | 10/2012 | McGinnis |
| 2013/0048564 | A1 | 2/2013 | Stewart et al. |
| 2016/0002073 | A1 | 1/2016 | Nowosielski-Slepowron |
| 2016/0016116 | A1 | 1/2016 | Ge et al. |
| 2017/0173536 | A1 | 6/2017 | Nagata et al. |
| 2018/0028977 | A1 | 2/2018 | Ghaffour et al. |
| 2020/0353415 | A1 | 11/2020 | Fujita et al. |

FOREIGN PATENT DOCUMENTS

| | | | | |
|---|---|---|---|---|
| JP | H11-075759 | A | 3/1999 | |
| JP | 2011-525147 | A | 9/2011 | |
| JP | 2016-155078 | A | 9/2016 | |
| JP | 2017-127842 | A | 7/2017 | |
| JP | 2018-008270 | A | 1/2018 | |
| JP | 6333573 | B | 5/2018 | |
| WO | 2009/155596 | A2 | 12/2009 | |
| WO | 2013/046961 | A1 | 4/2013 | |
| WO | 2013/170977 | A1 | 11/2013 | |
| WO | 2016/006670 | A1 | 1/2016 | |
| WO | 2016/210337 | A3 | 12/2016 | |
| WO | 2017/142494 | A1 | 8/2017 | |
| WO | 2019/098390 | A1 | 5/2019 | |
| WO | WO-2019134014 | A1 * | 7/2019 | .............. A23C 1/12 |
| WO | 2019/161444 | A1 | 8/2019 | |
| WO | WO-2020050282 | A1 * | 3/2020 | .............. A23L 5/51 |

OTHER PUBLICATIONS

Maguire-Boyle, Samuel J., and Andrew R. Barron. "Organic compounds in produced waters from shale gas wells." Environmental Science: Processes & Impacts 16.10 (2014): 2237-2248. (Year: 2014).*

Mia, Rony, et al. "Review on various types of pollution problem in textile dyeing & printing industries of Bangladesh and recommandation for mitigation." Journal of Textile Engineering & Fashion Technology 5.4 (2019): 220-226. (Year: 2019).*

Supplementary European Search Report in corresponding European Patent Application No. 208658822.9 dated Jun. 1, 2022.

International Search Report issued in corresponding International Patent Application No. PCT/JP2020/035322 dated Nov. 10, 2020.

International Preliminary Report on Patentability and Written Opinion issued in corresponding International Patent Application No. PCT/JP2020/035322 dated Mar. 31, 2022.

Office Action in the European Patent Application No. 20865822.9 dated Oct. 13, 2025.

Wang et al., "Integrated forward osmosis-membrane distillation (FO-MD) hybrid system for the concentration of protein solution," Chemical Engineering Science, 66 (11): 2421-2430 (2011).

Xie et al., "A Forward Osmosis-Membrane Distillation Hybrid Process for Direct Sewer Mining: System Performance and Limitations," Environmental Science & Technology, 47 (23): 13486-13493 (2013).

Environmental Sciences: Processes and Impacts, 16 (10): 2237-2248 (2014).

* cited by examiner

METHOD FOR CONCENTRATING RAW MATERIAL SOLUTION, AND SYSTEM FOR CONCENTRATING RAW MATERIAL SOLUTION

FIELD

The present invention relates to a concentration method and a concentration system for a feed solution containing water and an organic solvent as a solvent.

BACKGROUND

Among feed solutions requiring concentration, there are numerous industrial feed solutions containing water and an organic solvent as a solvent. In synthesis processes of substances comprising amino acid sequences such as peptides, enzymes, and proteins (hereinafter referred to as "the peptides"), the solvent in the feed solutions to be concentrated may contain both water and an organic solvent.

The peptides are widely used as diagnostic/test drugs and pharmaceuticals, and the feeds thereof are very expensive. Therefore, when concentrating feed solutions containing peptide, etc., it is important to recover the peptides in high yield without denaturation.

As one method for stably and efficiently concentrating feed solutions containing the peptides, a membrane filtration method using an ultrafiltration membrane is used. Since the membrane filtration method using an ultrafiltration membrane, which is a technique for separating a feed solution by sieving, does not involve a temperature change, it is possible to reduce energy load. In the membrane filtration method using an ultrafiltration membrane, components having a size larger than the cut-off molecular weight of the membrane are retained, but water passes through the membrane. Thus, this method is effective for concentrating the peptides (PTL 1).

A reverse osmosis (RO) method using a membrane which allows a solvent to permeate at a molecular level is known. The RO method is a method for concentrating a feed solution, configured such that the feed solution is pressurized to a predetermined pressure higher than the osmotic pressure of the feed solution and then supplied to an RO membrane module, where only the solvent in the feed solution permeates the RO membrane, thereby removing the solvent (typically water) in the feed solution (PTL 2).

As another concentration method for a feed solution, a forward osmosis (FO) method is known. The FO method is a concentration method for a feed solution, wherein a feed solution is brought into contact with a draw solution having a higher osmotic pressure than the feed solution via a forward osmotic (FO) membrane, and the solvent is diffused from the feed solution to the draw solution. Since the FO method does not require pressurization, it is expected that the solute contained in the feed solution can be efficiently concentrated without adhesion (PTL 3).

As yet another concentration method for a feed solution, membrane distillation (MD) methods are known. As one method of membrane distillation, the DCMD method (Direct Contact MD), in which a feed solution is concentrated by bringing the feed solution into contact with cooling water having a temperature lower than the feed solution and thereby transferring the vapor of the solvent in the feed solution from the feed solution to the cooling water, is well known (PTL 4).

PTL 5 discloses a method in which a forward osmosis method and membrane distillation are combined. In the technique of PTL 5, the membrane distillation method is used to regenerate the draw solution used in the forward osmosis method.

CITATION LIST

Patent Literature

[PTL 1] WO 2013/170977
[PTL 2] Japanese Unexamined Patent Publication (Kokai) No. 11-75759
[PTL 3] US 2016/0016116
[PTL 4] WO 2016/006670
[PTL 5] Japanese Unexamined Patent Publication (Kokai) No. 2017-127842

SUMMARY

Technical Problem

In the membrane filtration method using an ultrafiltration membrane described in PTL 1, since it is necessary to pressurize the feed solution, there is an issue where the adhesion of the solute contained in the feed solution to the membrane surface occurs, reducing the recovery rate. In the case of medium molecular weight drugs being developed these days, where the molecular weight is less than the cut-off molecular weight of the ultrafiltration membrane, the solute partially permeates the ultrafiltration membrane, thus reducing the recovery rate.

In the RO method described in PTL 2, since it is necessary to pressurize the feed solution, there is an issue where the adhesion of the solute contained in the feed solution to the membrane surface occurs, reducing the recovery rate. In the RO method, the osmotic pressure of the solvent (filtered solvent) in the concentrate feed solution does not exceed the pressure of the high-pressure pump used for pressurization, and thus the concentration rate of the feed solution by the RO method is limited by the ability of the pump.

In the forward osmosis process described in PTL 3, since the active layer of the forward osmotic membrane selectively passes water molecules during concentration, there is an issue where a large amount of organic solvent remains in the concentrate when a feed solution containing both water and an organic solvent as a solvent is concentrated.

In the membrane distillation method described in PTL 4, since a component having a low osmotic pressure is preferentially removed out of the system through the membrane, there is an issue where a large amount of water remains in the concentrate when a feed solution containing both water and an organic solvent as a solvent is concentrated. Additionally, when a large amount of water remains in the concentrate, there is an issue where an active component in the feed solution precipitates.

In the technique of PTL 5, the membrane distillation method is used to regenerate the draw solution used for forward osmosis and is not applied to concentrating the feed solution.

An object of the present invention is to provide a concentration method and a concentration system for a feed solution, which are capable of concentrating a feed solution without the conditions of pressurization and heating and capable of controlling the ratio of water and an organic solvent in the feed solution after concentrating to any ratio.

Solution to Problem

The present invention has been made to achieve the above object.

The present inventors have discovered that when concentrating a feed solution containing water and an organic solvent as a solvent, by combining a concentration method of removing mainly water in the feed solution and a concentration method of removing mainly the organic solvent, the ratio of water and the organic solvent can be adjusted to any ratio, thus arriving at the present invention.

The present invention is described as follows:

<<Aspect 1>> A concentration method for a feed solution containing a solute and a solvent to obtain a concentrate of the feed solution, wherein the solvent contains water and an organic solvent, and
the concentration method comprises a combination of
a first concentration method of removing water in the feed solution by a forward osmosis method, and
a second concentration method of removing water and the organic solvent in the feed solution through evaporation.

<<Aspect 2>> The concentration method for a feed solution according to Aspect 1, wherein the concentration method of removing water and the organic solvent in the feed solution through evaporation is a membrane distillation method.

<<Aspect 3>> The concentration method for a feed solution according to Aspect 1 or 2, wherein the second concentration method is carried out after the first concentration method.

<<Aspect 4>> The concentration method for a feed solution according to Aspect 1 or 2, wherein the first concentration method is carried out after the second concentration method.

<<Aspect 5>> The concentration method for a feed solution according to any one of Aspects 1 to 4, wherein at least one of a solute concentration and a solvent composition in the concentrate of the feed solution is measured online, and execution, change in concentrating rate, or suspension of the first concentration method and the second concentration method is determined in accordance with the measured value.

<<Aspect 6>> The concentration method for a feed solution according to Aspect 5, wherein at least one of the solute concentration and the solvent composition in the concentrate of the feed solution is measured by one or more measuring means selected from the group consisting of specific gravity measurement, pH measurement, conductivity measurement, liquid level measurement, optical rotation measurement, near-infrared spectroscopic analysis, and weight measurement of the concentrate.

<<Aspect 7>> The concentration method for a feed solution according to any one of Aspects 1 to 6, wherein the solvent is a mixture containing water and
one or more selected from the group consisting of acetonitrile, methanol, ethanol, and isopropanol.

<<Aspect 8>> The concentration method for a feed solution according to any one of Aspects 1 to 7, wherein the solute is one or more selected from the group consisting of an amino acid, a peptide, a protein, a saccharide, a vaccine, a nucleic acid, an antibiotic, an antibody-drug conjugate (ADC), and a vitamin.

<<Aspect 9>> The concentration method for a feed solution according to any one of Aspects 1 to 8, wherein the solute has a number-average molecular weight of 100 to 50,000.

<<Aspect 10>> The concentration method for a feed solution according to any one of Aspects 1 to 9, wherein the temperature of the feed solution is regulated to a range of 1° C. to 50° C.

<<Aspect 11>> The concentration method for a feed solution according to any one of Aspects 1 to 10, wherein an alcohol selected from methanol, ethanol, isopropanol, and t-butanol is used as a solute of a draw solution used in the forward osmosis method.

<<Aspect 12>> The concentration method for a feed solution according to any one of Aspects 1 to 11, wherein when at least one of the first concentration method and the second concentration method is carried out,
a solid-liquid separation step of filtering the feed solution is carried out.

<<Aspect 13>> A concentration system for a feed solution by concentrating a feed solution containing a solute and a solvent to obtain a concentrate of the feed solution, wherein the solvent contains water and an organic solvent, and
the concentration system comprises a combination of
a first concentrating means of removing water in the feed solution by a forward osmosis method, and
a second concentrating means of removing water and the organic solvent in the feed solution through evaporation.

<<Aspect 14>> The concentration system for a feed solution according to Aspect 13, wherein the concentrating means of removing water and the organic solvent in the feed solution through evaporation is a membrane distillation method.

<<Aspect 15>> The concentration system for a feed solution according to Aspect 13 or 14, wherein the second concentrating means is arranged after the first concentrating means.

<<Aspect 16>> The concentration system for a feed solution according to Aspect 13 or 14, wherein the first concentrating means is arranged after the second concentrating means.

<<Aspect 17>> The concentration system for a feed solution according to any one of Aspects 13 to 16, wherein the system comprises a measuring means of measuring at least one of a solute concentration and a solvent composition in the concentrate of the feed solution online, and operation, change in concentrating rate, or suspension of the first concentrating means and the second concentrating means is determined in accordance with a value measured by the measuring means.

<<Aspect 18>> The concentration system for a feed solution according to Aspect 17, wherein the measuring means of measuring at least one of the solute concentration and the solvent composition in the concentrate of the feed solution is one or more measuring means selected from the group consisting of specific gravity measurement, pH measurement, conductivity measurement, liquid level measurement, optical rotation measurement, near-infrared spectroscopic analysis, and weight measurement of the concentrate.

<<Aspect 19>> The concentration system for a feed solution according to any one of Aspects 13 and 18, wherein the solvent is a mixture containing water and
one or more selected from the group consisting of acetonitrile, methanol, ethanol, and isopropanol.

<<Aspect 20>> The concentration system for a feed solution according to any one of Aspects 13 to 19, wherein the solute is one or more selected from the group consisting of an amino acid, a peptide, a protein, a saccharide, a vaccine, a nucleic acid, an antibiotic, and a vitamin.

<<Aspect 21>> The concentration system for a feed solution according to any one of Aspects 13 to 20, wherein the solute has a number-average molecular weight of 100 to 50,000.

<<Aspect 22>> The concentration system for a feed solution according to any one of Aspects 13 to 21, wherein the temperature of the feed solution is regulated to a range of 1° C. to 50° C.

<<Aspect 23>> The concentration system for a feed solution according to any one of Aspects 13 to 22, wherein an alcohol selected from methanol, ethanol, and isopropanol is used as a solute of a draw solution used in the forward osmosis method.

<<Aspect 24>> A concentration apparatus for concentrating a feed solution containing a solute and a solvent to obtain a concentrate of the feed solution, wherein a feed solution tank for storing the feed solution is connected to
a first concentrating unit for concentrating the feed solution by a forward osmosis method, and
a second concentrating unit for concentrating the feed solution by removing water and an organic solvent in the feed solution through evaporation.

<<Aspect 25>> A concentration apparatus for concentrating a feed solution containing a solute and a solvent to obtain a concentrate of the feed solution, wherein a feed solution tank for storing the feed solution is connected to
a first concentrating unit for concentrating the feed solution by a forward osmosis method, and
a second concentrating unit for concentrating the feed solution by a membrane distillation method.

<<Aspect 26>> The apparatus according to Aspect 24 or 25, wherein at least one of a solute concentration and a solvent composition of the feed solution in the feed solution tank is measured online, and operation, change in concentrating rate, or suspension of the first concentrating unit and the second concentrating unit is automatically determined in accordance with the measured solvent composition.

<<Aspect 27>> The apparatus according to any one of Aspects 24 to 26, wherein the feed solution tank comprises a filter and a feed solution filtration pipe,
the filter is mounted higher than a surface of the feed solution in the feed solution tank,
the feed solution filtration pipe comprises an inlet at a bottom portion of the feed solution and an outlet at an upper portion of the filter, and
the feed solution is delivered from the bottom portion of the feed solution tank to the upper portion of the filter via the feed solution filtration pipe, passes through the filter, and flows into the feed solution in the feed solution tank.

<<Aspect 28>> The apparatus according to any one of Aspects 24 to 26, wherein an inner portion of the feed solution tank is divided into a first chamber and a second chamber by a partition plate,
the apparatus comprises
a means of extracting the feed solution from a bottom portion of the first chamber to supply at least one of the first concentrating unit and the second concentrating unit;

a means of returning a concentrated feed solution obtained from at least one of the first concentrating unit and the second concentrating unit to the second chamber; and
a first chamber-second chamber connecting pipe connecting the first chamber and the second chamber,
the first chamber-second chamber connecting pipe comprises
a plurality of valves connected at different heights in the second chamber; and
an outlet opening into a bottom portion of the first chamber, and
the feed solution in the second chamber is collected from at least one of the plurality of valves, passes through the first chamber-second chamber connecting pipe, and discharges from the outlet to return into the first chamber.

Advantageous Effects of Invention

According to the concentration method for a feed solution of the present invention, the feed solution can be concentrated without heating and pressurization, and the solvent composition can be adjusted during concentration. Therefore, solvent replacement after the concentrating step is not necessary, and a closed-system apparatus can be configured so that the loss of feed components is small and the concentration treatment can be carried out in a short time.

When the concentration apparatus of the present invention is used, a concentration system for a feed solution having the advantages as described above can be constructed.

DESCRIPTION OF EMBODIMENTS

<<Concentration System for Feed Solution>>

The concentration system for a feed solution of the present invention is a concentration system for a feed solution by concentrating a feed solution containing a solute and a solvent to obtain a concentrate of the feed solution, wherein the solvent contains water and an organic solvent, and the concentration system comprises a combination of a first concentrating means of removing water in the feed solution by a forward osmosis method, and a second concentrating means of removing water and the organic solvent in the feed solution through evaporation.

The above first concentrating means is carried out by a forward osmosis method. Of water and the organic solvent, water, which has a smaller molecular size, tends to be preferentially removed in the forward osmosis method of the first concentrating means.

The second evaporating means is carried out by a method of removing the solvent through evaporation. Of water and the organic solvent, the one having a higher vapor pressure is preferentially removed in the second concentrating means. The proportion of the organic solvent removed is generally higher.

Thus, the concentration system of the present invention, carried out as a combination of these means, not only simply carries out concentration, but can carry out concentration while optionally controlling the ratio of water and the organic solvent in the solvent in the feed solution to be concentrated.

Hereinafter, preferred embodiments of the present invention will be specifically described in detail as non-limiting examples.

<First Concentrating Means>

The first concentrating means in the concentration system for a feed solution of the present invention is a forward osmosis method that uses a forward osmotic membrane.

Figure 1:
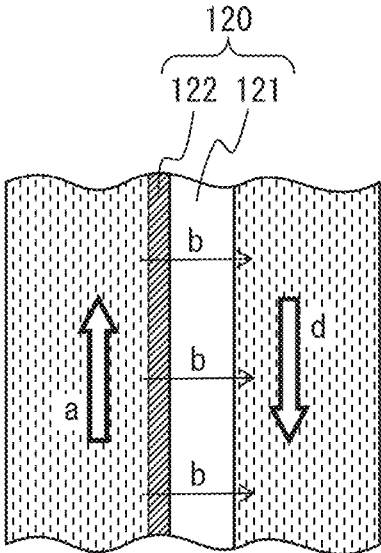
FIG. 1 is a schematic diagram for describing the action mechanism of a forward osmosis method used in the concentration system for a feed solution of the present invention.

FIG. 1 is a schematic diagram showing the action mechanism of the concentration method that uses a forward osmotic membrane.

In FIG. 1, a forward osmotic membrane (120) makes contact with a feed solution (a) on one side of the membrane and with a draw solution (d) having a higher osmotic pressure than the feed solution on the opposite side. The forward osmotic membrane (120) of FIG. 1 comprises a substrate layer (121) and an active layer (122) formed on one side of the substrate layer (121). The active layer (122) has a very dense structure which is mainly permeable to water and is not permeable to a solute, and is formed on the surface of the substrate layer (121) on the side in contact with the feed solution (a).

As the material of the substrate layer (121), an ultrafiltration membrane is generally used. The draw solution (d) permeates a portion of the substrate layer (121), composed of the ultrafiltration membrane, of the forward osmotic membrane (120), and the feed solution (a) is brought into contact with the draw solution (d) via the active layer (122). In this case, a solvent, mainly water, in the feed solution (a) is transferred to the side of the draw solution (d) having a higher osmotic pressure, and concentration is carried out.

The form of the forward osmotic membrane may be any of, for example, a hollow-fiber membranous, a tubular, and a flat membranous structure. The hollow-fiber membranous forward osmotic membrane is suitable since a flow path through which the feed solution and the draw solution pass can be formed without using a spacer, and uniform concentration can be carried out.

The material of the ultrafiltration membrane constituting the substrate layer can be selected from materials that are widely used. However, a material that dissolves or swells in an organic solvent in the solvent contained in the feed solution and cannot maintain pore shape of the membrane cannot be used.

The material of the ultrafiltration membrane preferably has a thin membrane layer composed of at least one selected from the group consisting of, for example, polyethersulfone, polysulfone, polyketone, polyether ether ketone, polyphenylene ether, polyvinylidene fluoride, polyacrylonitrile, polyimine, polyimide, polybenzoxazole, polybenzimidazole, sulfonated tetrafluoroethylene, and polyamide as a main component.

The material of the active layer mainly uses polyamide. The active layer composed of polyamide can be formed by interfacial polymerization of a polyfunctional acid halide and a polyfunctional aromatic amine on the substrate layer.

The polyfunctional aromatic acid halide is an aromatic acid halide compound having two or more acid halide groups in one molecule. Specific examples thereof include a trimesic acid halide, a trimellitic acid halide, an isophthalic acid halide, a terephthalic acid halide, a pyromellitic acid halide, a benzophenonetetracarboxylic acid halide, a biphenyldicarboxylic acid halide, a naphthalenedicarboxylic acid halide, a pyridinedicarboxylic acid halide, and a benzene-disulfonic acid halide, which can be used alone or in a mixture thereof. Examples of the halide ion in the aromatic acid halide compounds include chloride ion, bromide ion, and iodide ion. In the present invention, particularly trimesic acid chloride alone, a mixture of trimesic acid chloride and isophthalic acid chloride, or a mixture of trimesic acid chloride and terephthalic acid chloride is preferably used.

The polyfunctional aromatic amine is an aromatic amine compound having two or more amine groups in one molecule. Specific examples thereof include m-phenylenediamine, p-phenylenediamine, 3,3'-diaminodiphenylmethane, 4,4'-diaminodiphenylamine, 4,4'-diaminodiphenyl ether, 3,4'-diaminodiphenyl ether, 3,3'-diaminodiphenylamine, 3,5-diaminobenzoic acid, 4,4'-diaminodiphenyl sulfone, 3,3'-diaminodipheny sulfone, 3,4'-diaminodiphenyl sulfone, 1,3,5-triaminobenzene, and 1,5-diaminonaphthalene, which can be used alone or in a mixture thereof. In the present invention, particularly one or more selected from m-phenylenediamine and p-phenylenediamine are preferably used.

The interfacial polymerization of the polyfunctional acid halide and the polyfunctional aromatic amine can be carried out according to a conventional method.

When a hollow-fiber forward osmotic membrane is used, the outer diameter of the hollow-fiber membrane is, for example, 300 µm to 5,000 µm, preferably 350 µm to 4,000 µm. The inner diameter of the hollow-fiber membrane is, for example, 200 µm to 4,000 µm, preferably 250 µm to 1,500 µm. Although the reason is not certain, when the inner diameter of the hollow fiber is less than 200 µm, the pressure in the hollow fiber during circulation operation becomes large and the contact area of the feed component becomes large. Therefore, the solute contained in the feed solution is likely to adhere to the membrane surface. When the inner diameter of the hollow fiber is greater than 4,000 µm, the contact area of the feed component becomes excessively small, and the separation efficiency of the solvent and the solute may be impaired.

As the draw solution used in the forward osmosis method, a solution containing one or more selected from the group consisting of inorganic salts such as sodium chloride, magnesium chloride, calcium chloride, sodium sulfate, magnesium sulfate, and potassium sulfate; citrates such as sodium citrate and magnesium citrate; acetates such as sodium acetate and magnesium acetate; hydroxycarboxylic acids such as gluconic acid, lactic acid, glycolic acid, and glyceric acid; organic salts such as metallic salts thereof, organic solvents; and solid organic substances at room temperature as solutes can be used.

The organic solvent used as a solute is typically an alcohol, and is preferably methanol, ethanol, isopropanol, or t-butanol, and is particularly preferably isopropanol. Isopropanol has an appropriate vapor pressure and does not azeotrope with water, and thus can be easily removed from the feed solution by a second concentration method comprising an evaporating means, even when mixed into the feed solution during concentration. Thus, it is preferable that the feed solution be, for example, a pharmaceutical product or a pharmaceutical feed, from the viewpoint of obtaining a high-purity concentrate.

Examples of the solvent of the draw solution include water and alcohols, and may be one or more selected from thereamong. Examples of the alcohol include polyhydric alcohols such as monohydric alcohols, dihydric alcohols, trihydric alcohols, tetrahydric alcohols, pentahydric alcohols, and hexahydric alcohols; glyercin, t-butyl alcohol, isopropanol, xylitol, sorbitol, mannitol, perseitol, volemitol, and D-erythro-D-galacto-octitol.

The solvent of the draw solution is typically water.

As described above, an alcohol can be used as a solute and a solvent of the draw solution.

When an alcohol is used as the solute of the draw solution, the solvent of the draw solution is preferably water. In this case, the draw solution is particularly preferably an aqueous solution of isopropanol.

When an alcohol is used as the solvent of the draw solution, the solute of the draw solution is preferably a hydroxycarboxylic acid or a solid organic substance at room temperature.

Since the driving force for moving the solvent from the feed solution to the draw solution in the forward osmosis method is the osmotic pressure difference between the feed solution and the draw solution, it is necessary to renew the liquid between the active layer of the forward osmotic membrane and the interface of the feed solution or the draw solution. Therefore, it is necessary to flow the feed solution and the draw solution at an appropriate flow rate.

In FIG. 1, the feed solution (a) and the draw solution (d) are opposing flows, but may be parallel flows.

Figure 3:
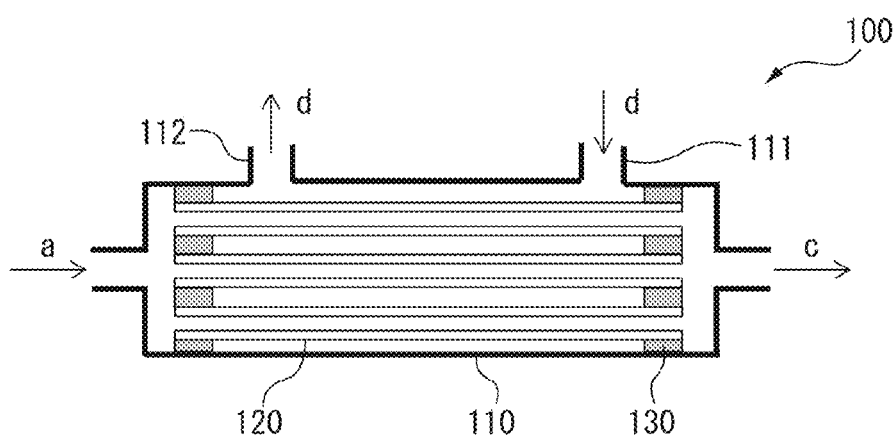
FIG. 3 is a schematic cross-sectional diagram for describing one example of the structure of a forward osmotic membrane module used in the concentration system for a feed solution of the present invention.

FIG. 3 is a schematic diagram showing one example of a forward osmotic membrane module, preferably applied as the first concentrating means of the concentration system for a feed solution of the present invention.

In the forward osmotic membrane module (100) of FIG. 3, a plurality of hollow-fiber forward osmotic membranes (120) are stored in a housing (110). Both ends of each forward osmotic membrane (120) are adhesively fixed to the housing (110) with an adhesive resin (130). Two housing side pipes are located on a side surface of the housing (110). Of the housing side pipes, one is the draw solution inlet (111) and the other is the draw solution outlet (112).

The interior of the housing (110) is split in two: a space through which the feed solution (a) flows and a space through which the draw solution (d) flows, by an outer wall of the forward osmotic membrane (120) and the adhesive resin (130). Except that the solvent can travel through an inner wall of the forward osmotic membrane (120), both spaces are fluidly shielded.

When a feed solution (a) is introduced from one end of the forward osmotic membrane module (100), the feed solution (a) flows into the inside of the membrane of the hollow-fiber forward osmotic membrane (120) and flows out from the other end surface.

When the draw solution (d) flows from the draw solution inlet (111) of the side pipes of the housing (110), the draw solution (d) flows into the inside space of the hollow-fiber forward osmotic membrane (120) and flows out from the draw solution outlet (112).

Subsequently, the feed solution (a) can be brought into contact with the draw solution (d) via the forward osmotic membrane (120). At this time, the solvent (mainly water) is transferred from the feed solution (a) to the draw solution (d) by the difference in osmotic pressure of the two liquids. Concentration is carried out by such a mechanism in the forward osmotic membrane method.

When the flow rate of the feed solution (a) and/or the flow rate of the draw solution (d) is large, the osmotic pressure particularly in the active layer of the forward osmotic membrane (120) becomes large, and thus the permeation amount of liquid per membrane area of the forward osmotic membrane becomes large.

The flow direction of the feed solution (a) and the flow direction of the draw solution (d) in the forward osmotic membrane module (100) of FIG. 3 are opposite, but may be parallel.

The material of the housing (110) of the forward osmotic membrane module (100) of FIG. 3 is selected from the viewpoint of chemical resistance, pressure resistance, heat resistance, impact resistance, and weather resistance, wherein components contained in the feed solution (a) and the draw solution (d) do not deteriorate various performances. For example, a resin or a metal can be used as the material of the housing (110). From the above viewpoint, it is preferable to select a resin such as polypropylene, polysulfone, polyethersulfone, polyvinylidene fluoride, ABS resin, a fiber-reinforced plastic, or vinyl chloride; or a metal such as stainless steel, brass, or titanium.

As the adhesive resin (130) in FIG. 3, it is desirable to have satisfactory mechanical strength and heat resistance at 100° C. Examples of the resin which can be used as the adhesive resin (130) include a thermosetting epoxy resin and a thermosetting urethane resin. From the viewpoint of heat resistance, an epoxy resin is preferable. From the viewpoint of handleability, a urethane resin is preferable.

The method of adhesively fixing the forward osmotic membrane (120) to the housing (110) may be a known bonding method relating to the production of a hollow-fiber membrane module.

<Second Concentrating Means>

The first concentrating means in the concentration system for a feed solution of the present invention is a concentrating means of removing water and an inorganic solvent in the feed solution through evaporation.

Examples of such a concentrating means include an evaporator, a thin-membrane distillation apparatus, a method of flowing a gas into a container charged with the feed solution to transfer the solvent out of the container, and a membrane distillation method. Among these, a membrane distillation method facilitates the adjustment of the ratio of water and the organic solvent removed from the feed solution, and is thus a particularly effective concentrating means.

(Membrane Distillation Method)

Figure 2:
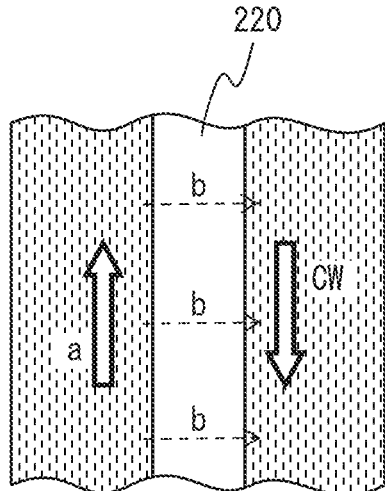
FIG. 2 is a schematic diagram for describing the action mechanism of a membrane distillation method used in the concentration system for a feed solution of the present invention.

FIG. 2 is a schematic diagram showing the action mechanism of the concentration method that uses a membrane distillation method.

In FIG. 2, a membrane (220) for membrane distillation comes into contact with the feed solution (a) on one side of the membrane and a cooling water (CW) having a temperature lower than the feed solution (a) on the opposite side. In the membrane distillation method, the temperature of the feed solution (a) is higher, and thus the solvent (b) has a higher vapor pressure. The solvent (b) in the feed solution (a) evaporates to form vapor, and is transferred to the cooling water (CW) side via the membrane (220) for membrane distillation to be liquefied, thereby facilitating concentration.

In the membrane distillation method, both water and the organic solvent in the solvent (b) of the feed solution (a) are removed through evaporation. However, of these, the one having a higher vapor pressure is preferentially removed. Of water and an organic solvent, the organic solvent generally has a higher vapor pressure, and thus the proportion of the organic solvent removed is higher.

As another embodiment of the membrane distillation method, in place of bringing the feed solution (a) and the cooling water (CW) into contact with each other via the membrane, a VMD (Vacuum MD) method, in which vapor is extracted by putting the feed solution (a) and the opposite side of the membrane in a reduced pressure state, can be applied.

It is necessary for the membrane for membrane distillation to allow only the vapor of the solvent, not the feed solution, to pass therethrough. In the case of the feed solution having a high proportion of the organic solvent in the solvent, since the surface tension of the feed solution is low, the feed solution enters the pores of the membrane for membrane distillation and flows to the cooling water side as-is, and so-called "wetting" may occur. When wetting occurs, the membrane for membrane distillation loses the concentrating function thereof. In order to avoid this, a highly hydrophobic membrane is used as the membrane for membrane distillation.

A water contact angle is used as a method to express hydrophobicity. In this method, hydrophobicity is evaluated by the contact angle between a water droplet disposed on a surface of the membrane and the membrane. The membrane for the membrane distillation method used as the second concentrating means of the present invention preferably has a water contact angle of 90° or greater, more preferably 110° or greater, and even more preferably 120° or greater. There is no upper limit to the water contact angle, but realistically the upper limit is about 150°.

Since membrane distillation is preferably carried out at near room temperature, the distillation is carried out at a low vapor pressure compared to high-temperature distillation. Therefore, as the property of the membrane for membrane distillation in the present invention, it is necessary for the vapor permeation resistance to be as low as possible. From this viewpoint, the pores of the membrane for membrane distillation are preferably as large as possible without wetting. The average pore size is preferably in the range of 0.02 μm to 0.5 μm, more preferably 0.05 μm to 0.3 μm. When the average pore size of the membrane for membrane distillation is less than 0.02 μm, the vapor permeation resistance is too high and a long concentrating time is required. When the value is greater than 0.5 μm, the possibility of wetting becomes high and stable concentration cannot be carried out.

For the shape of the membrane for membrane distillation, any of a hollow-fiber membranous, a tubular, and a flat membranous shape can be applied.

The porosity of the membrane for membrane distillation is preferably 60% or greater, more preferably 70% or greater, from the viewpoint of obtaining high vapor permeability. For the strength of the membrane itself to be satisfactorily maintained and issues such as rupture to be less likely to occur in long-term use, the porosity is preferably 90% or less, more preferably 85% or less.

When a hollow-fiber membranous membrane for membrane distillation is used, the membrane thickness is preferably 10 μm to 1,000 μm, more preferably 20 μm to 500 μm, from the viewpoint of achieving both vapor permeability and mechanical strength of the membrane. When the membrane thickness is 1,000 μm or less, high vapor permeability can be obtained. When the membrane thickness is 10 μm or greater, the membrane can be used without deformation.

The outer diameter of the hollow-fiber membranous membrane for membrane distillation is preferably 300 μm to 5,000 μm, more preferably 350 μm to 4,000 μm, and the inner diameter is preferably 200 μm to 4,000 μm, more preferably 250 μm to 3,000 μm. When the hollow-fiber membrane is set to the sizes in these ranges, the balance of membrane strength and effective area of the membrane becomes satisfactory.

The material of the membrane for membrane distillation can be selected from ones comprising at least one resin selected from the group consisting of polysulfone, polyethersulfone, polyethylene, polypropylene, polyvinylidene fluoride, polytetrafluoroethylene, an ethylene/tetrafluoroethylene copolymer, and polychlorotrifluoroethylene. From the viewpoint of hydrophobicity, membrane formability, and mechanical and thermal durability, it is preferable to select and use polyvinylidene fluoride, an ethylene/tetrafluoroethylene copolymer, and polychlorotrifluoroethylene.

In order to further improve the hydrophobicity of the membrane for membrane distillation, a membrane for membrane distillation having a hydrophobic polymer attached to at least a portion thereof can be used. The hydrophobic polymer may be, for example, a polymer having a hydrophobic structure. Examples of the hydrophobic structure include a non-polar group or a weakly polar group, and a non-polar skeleton or a weakly polar skeleton. Examples of the non-polar group or the weakly polar group include a hydrocarbon group and a fluorine-containing group. Examples of the non-polar skeleton or the weakly polar skeleton include a hydrocarbon backbone and a siloxane backbone.

Examples of such hydrophobic polymer include a polymer having a siloxane bond and a fluorine atom-containing polymer, and more specifically include the following:

(A) the polymer having a siloxane bond may be, for example, a dimethyl silicone gel, a methylphenyl silicone gel, a reactive modified silicone gel having an organic functional group (amino group, fluoroalkyl group, etc.), a silicone-based polymer which reacts with a silane coupling agent to form a crosslinked structure, and polymer gels which are crosslinked products thereof; and (B) the fluorine atom-containing polymer may be a polymer having a fluorine atom-containing group in a side chain, wherein the fluorine-atom containing group is a (per)fluoroalkyl group, a (per)fluoropolyether group, an alkylsilyl group, a fluorosilyl group, etc.

Specifically, the hydrophobic polymer is preferably a polymer of a (meth)acrylate-based monomer and/or a vinyl-based monomer, having a (per)fluoroalkyl group and/or a (per)fluoropolyether group having 1 to 12 carbon atoms.

Figure 4:
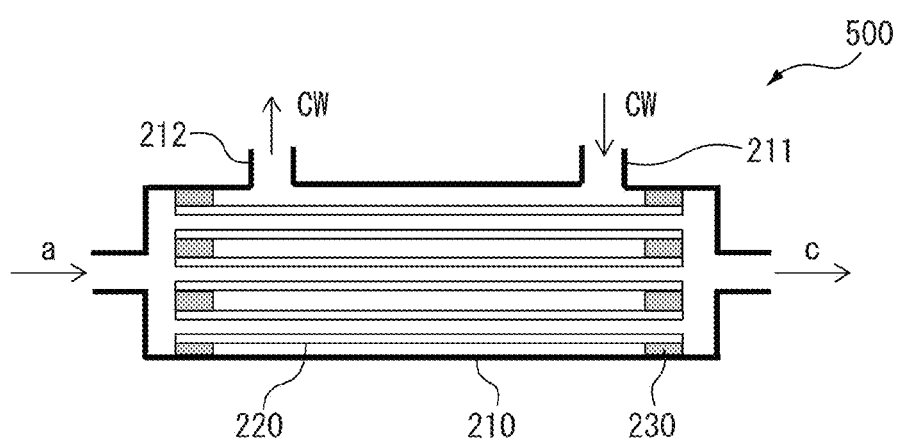
FIG. 4 is a schematic cross-sectional diagram for describing one example of the structure of a membrane module for membrane distillation used in the concentration system for a feed solution of the present invention.

FIG. 4 is a schematic diagram showing one example of a membrane module for membrane distillation, preferably applied as the second concentrating means of the concentration system for a feed solution of the present invention.

In the membrane module (500) for membrane distillation of FIG. 4, a plurality of hollow-fiber membranes (220) for membrane distillation are stored in a housing (210). Both ends of each membrane (220) for membrane distillation are adhesively fixed to the housing (210) with an adhesive resin (230). Two housing side pipes are located on a side surface of the housing (210). Of the housing side pipes, one is the cooling water inlet (211) and the other is the cooling water outlet (212).

The interior of the housing (210) is split in two: a space through which the feed solution (a) flows and a space through which the cooling water (CW) flows, by an outer wall of the membrane (220) for membrane distillation and the adhesive resin (230). Except that the solvent can travel through an inner wall of the membrane (220) for membrane distillation, both spaces are fluidly shielded.

When a feed solution (a) is introduced from one end of the membrane module (500) for membrane distillation, the feed solution (a) flows into the inside of the membrane of the hollow-fiber membrane (220) for membrane distillation and flows out from the other end surface.

When the cooling water (CW) flows from the cooling water inlet (211) of the side pipes of the housing (210), the cooling water (CW) flows into the outside space of the hollow-fiber membrane (220) for membrane distillation and flows out from the cooling water outlet (212).

Thus, the feed solution (a) can be brought into contact with the cooling water (CW) via the membrane for membrane distillation (120). Vapor of the solvent is transferred from the feed solution (a) to the cooling water (CW) by the difference in osmotic pressure of the two liquids and liquefied in the cooling water (CW), and the feed solution (a) is concentrated thereby.

In the membrane distillation method, both water and the organic solvent of the solvent (b) in the feed solution (a) evaporate, pass through the membrane (220) for membrane distillation as vapor, and are transferred to the cooling water (CW). The ratio of the moving water and the organic solvent is determined by the magnitude of the vapor pressures of both thereof, and normally the organic solvent is preferentially transferred, as described above.

When the flow rate of the feed solution (a) and/or the flow rate of the cooling water (CW) is large, the temperature difference between the feed solution (a) and the cooling water (CW) can be maintained, and thus the permeation amount of vapor per membrane area of the membrane for membrane distillation becomes large.

The flow direction of the feed solution (a) and the flow direction of the cooling water (CW) in the membrane module (500) for membrane distillation of FIG. 4 are opposite, but may be parallel.

The temperatures of the feed solution (a) and the cooling water (CW) are not particularly limited, but are preferably set to ranges that do not change the composition of the solute of the feed solution (a).

The material of the housing (210) of the membrane module (500) for membrane distillation of FIG. 4 is selected from the viewpoint of chemical resistance, pressure resistance, heat resistance, impact resistance, and weather resistance, wherein components contained in the feed solution (a) and the cooling water (CW) do not deteriorate various performances. For example, a resin or a metal can be used as the material of the housing (210). From the above viewpoint, it is preferable to select a resin such as polypropylene, polysulfone, polyethersulfone, polyvinylidene fluoride, ABS resin, a fiber-reinforced plastic, or vinyl chloride; or a metal such as stainless steel, brass, or titanium.

As the adhesive resin (230) in FIG. 4, it is desirable to have satisfactory mechanical strength and heat resistance at 100° C. Examples of the resin which can be used as the adhesive resin (230) include a thermosetting epoxy resin and a thermosetting urethane resin. From the viewpoint of heat resistance, an epoxy resin is preferable. From the viewpoint of handleability, a urethane resin is preferable.

The method of adhesively fixing the membrane (220) for membrane distillation to the housing (210) may be a known bonding method relating to the production of a hollow-fiber membrane module.

<<Embodiment of Concentration System for Feed Solution>>

FIGS. 5 to 10 show concentration systems of the present invention.

Figure 5:
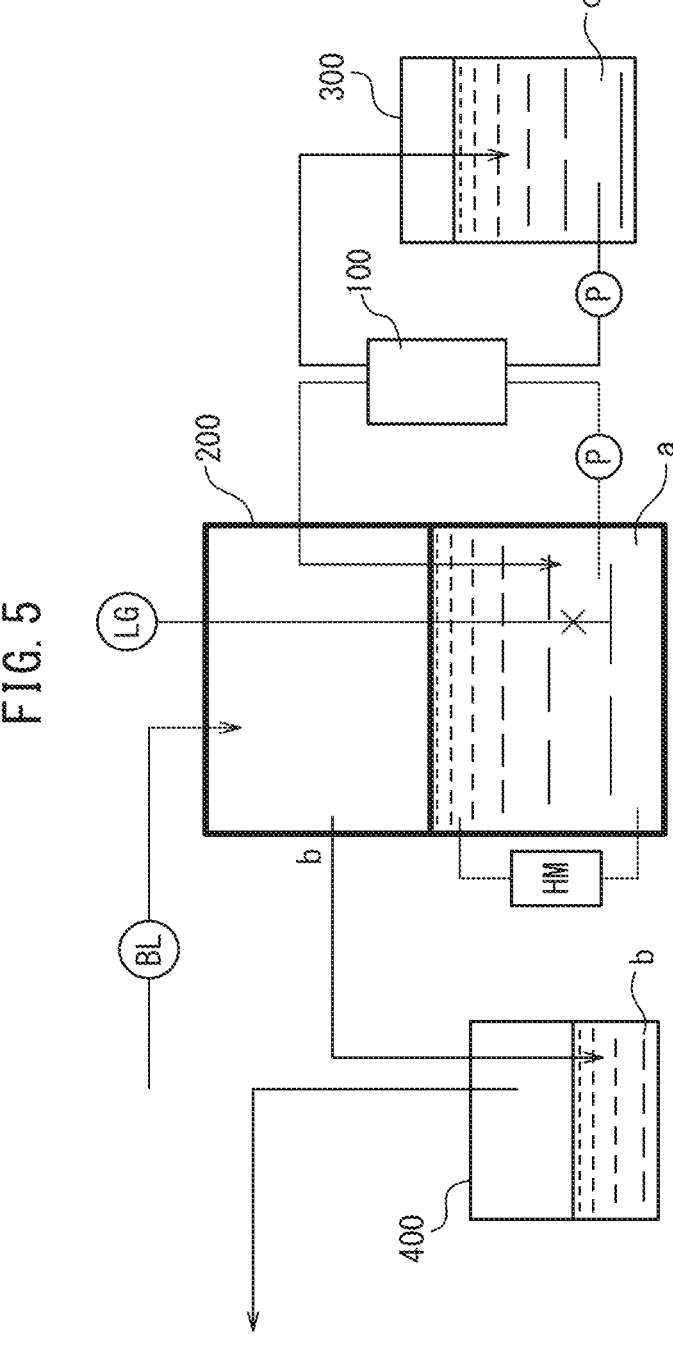
FIG. 5 is a schematic diagram for describing one example of the concentration system for a feed solution of the present invention.

The concentration system of FIG. 5 is an example in which a method of flowing a gas into a container charged with the feed solution to transfer the solvent out of the container is applied as the second concentrating means.

The system of FIG. 5 comprises a forward osmotic membrane module (100), a feed solution tank (200), a draw solution tank (300), and a trap (400), wherein the feed solution tank (200) is mounted with a blower (BL).

In the system of FIG. 5, the feed solution (a) is sent at a suitable flow rate by a pump (P) from a lower portion of the feed solution tank (200) filled with the feed solution (a) to one of the spaces (for example, a space on the side of the hollow-fiber forward osmotic membrane) of the forward osmotic membrane module (100). The flow rate of the feed solution (a) is manually or automatically regulated by a flow meter (not shown). The draw solution (d) is supplied by a pump (P) from the draw solution tank (300) filled with the draw solution (d) to another space (for example, an outside space of the hollow-fiber forward osmotic membrane) of the forward osmotic membrane module (100). Due to the difference in osmotic pressure between the feed solution (a) and the draw solution (d), a portion of the solvent (b) (mainly water) is transferred to the draw solution (d) side, and concentration occurs. The concentrated feed solution (a) exits from the forward osmotic membrane module (100) and is returned to the feed solution tank (200) to be circulated.

Because the concentration of the draw solution (d) is reduced by mixing with the solvent from the feed solution (a), in order to maintain the osmotic pressure of the draw solution (d) in continuous operation, it is necessary to successively renew the draw solution (d) or regenerate the draw solution (d) with an apparatus having the function of removing the transferred solvent therefrom. The regeneration apparatus is not shown in FIG. 5.

In the concentration by the forward osmotic membrane module (100), since water, which has a small molecular size, is mainly transferred to the draw solution (d) side, the composition of the solvent (b) in the feed solution (a) after concentration generally has a high proportion of the organic solvent.

In the system of FIG. 5, a blower (BL) is provided in the feed solution tank (200), and air is sent into the feed solution tank (200) by the blower. The introduced air and the solvent vapor evaporated by the air are discharged out of the feed solution tank (200), thereby facilitating concentration.

It is possible for the solvent vapor discharged from the feed solution tank (200) to be reliquefied and recovered by the trap (400).

According to the method of blowing air into the feed solution tank (200), since concentration occurs at the liquid surface of the feed solution (a), concentration with a stable composition can be carried out by providing the feed solution tank (200) with a stirring function as needed.

In the concentration by the second concentrating means, both water and the organic solvent are removed. However, the organic solvent having a high vapor pressure is preferentially removed, and thus the composition of the solvent (b) in the feed solution (a) after concentration generally has a high proportion of water.

Figure 6:
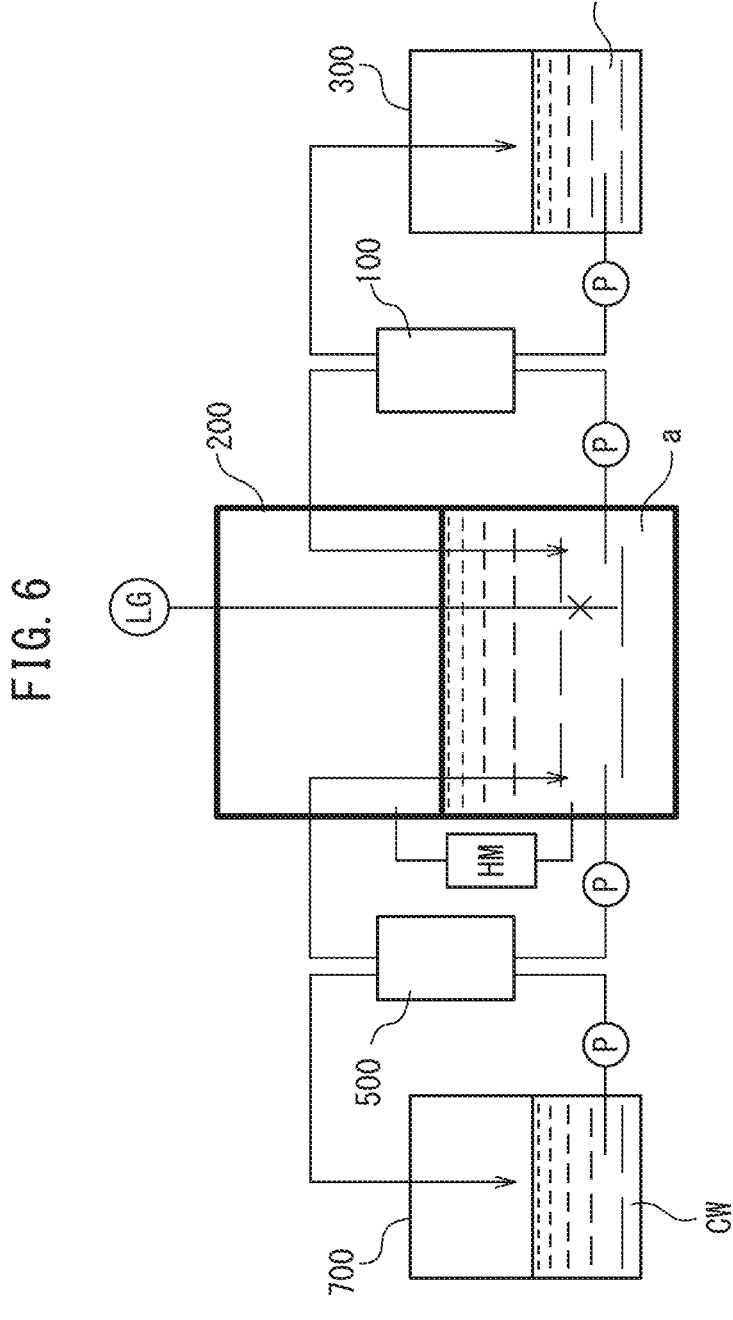
FIG. 6 is a schematic diagram for describing another example of the concentration system for a feed solution of the present invention.

The concentration system of FIG. 6 is an example in which a membrane distillation method is applied as the second concentrating means.

The system of FIG. 6 comprises a forward osmotic membrane module (100), a feed solution tank (200), a draw solution tank (300), a membrane module (500) for membrane distillation, and a cooling water tank (700).

In the concentration system of FIG. 6, the forward osmotic membrane module (100) and the membrane module (500) for membrane distillation are connected in parallel to the feed solution tank (200).

Concentration by the forward osmotic membrane module (100) is carried out by the same method as the system for concentration of FIG. 5.

In the concentration by the membrane module (500) for membrane distillation, the feed solution (a) is supplied at a suitable flow rate using a pump (P) from the bottom portion of the feed solution tank (200) to one of the spaces (for example, a space of the inside of the hollow-fiber membrane for membrane distillation) of the membrane module (500) for membrane distillation. The feed solution (a) is returned to the feed solution tank (200) to be circulated after passing through the interior of the hollow-fiber membrane. The return site is located at the bottom portion of the feed solution tank (200). It is preferable to set the site far from the site at which the membrane module (500) for membrane distillation is supplied, from the viewpoint of suppressing excessive concentration of the feed solution (a) and preventing loss of the solute in the concentrated feed solution (a) on the wall surface of feed solution tank (200).

Cooling water (CW) having a temperature lower than that of the feed solution (a) is introduced into another space (for example, an outside space of the hollow-fiber membrane for membrane distillation) of the membrane module (500) for membrane distillation.

Subsequently, the feed solution (a) is brought into contact with the cooling water (CW) via the hollow-fiber membrane for membrane distillation. The solvent in the feed solution (a) evaporates due to the difference in vapor pressure between the feed solution (a) and the cooling water (CW), passes through the membrane for membrane distillation as vapor, and is transferred to the cooling water (CW) side, thereby facilitating concentration. Since it is necessary to make a temperature difference between the feed solution (a) and the cooling water (CW), it is necessary for both the feed solution (a) from the feed solution tank (200) and the cooling water (CW) from the cooling water tank (700) to undergo heat exchange with a thermostatic tank, etc. to set the respective temperatures. These mechanisms are not shown in FIG. 6.

Since the volume of the cooling water (CW) is increased by mixing with the solvent from the feed solution (a), it is necessary that the cooling water tank (700) be sufficiently large or measures such as discharging a portion of the cooling water out of the tank via an overflow be taken. These mechanisms are not shown in FIG. 6.

The concentration by the membrane module (500) for membrane distillation facilitates the removal of the organic solvent, which has a high vapor pressure. Therefore, the composition of the solvent (b) in the feed solution (a) generally has a high proportion of water.

Figure 7:
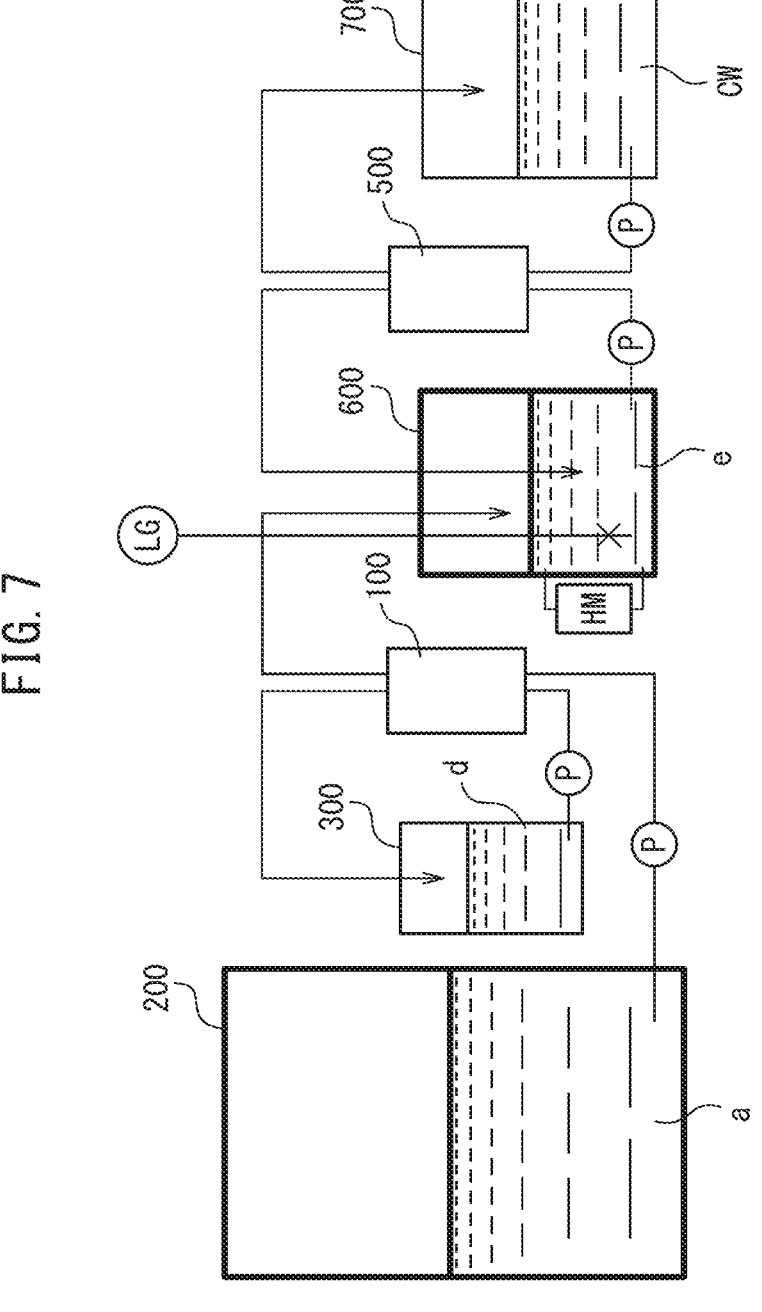
FIG. 7 is a schematic diagram for describing yet another example of the concentration system for a feed solution of the present invention.

The concentration system of FIG. 7 is another embodiment in which a membrane distillation method is applied as a second concentrating means, and is a system in which the second concentrating means is arranged after the first concentrating means.

In the concentration system of FIG. 7, the feed solution (a) is concentrated by the forward osmotic membrane module (100) as the first concentrating means, and the feed solution (a) concentrated by the forward osmotic membrane module (100) is delivered to a product tank (600). From the product tank (600), the feed solution (a) concentrated by the first concentrating means is supplied at a suitable flow rate by a pump (P) from the bottom portion of the tank to one of the spaces of the membrane module (500) for membrane distillation, and concentration by the membrane distillation method is carried out. The feed solution (a) concentrated by the membrane module (500) for membrane distillation is returned to the product tank (600) to be circulated.

The feed solution (a) after concentration, delivered from the forward osmotic membrane module (100) to the product tank (600), has a higher ratio of the organic solvent in the solvent (b). However, when the feed solution passes through the membrane module (500) for membrane distillation and is concentrated by the membrane distillation method, the proportion of water in the solvent (b) recovers.

In the system of FIG. 7, a hydrometer (HM) and a level gauge (LG) are mounted to the product tank (600). The hydrometer (HM) can be used to compare the specific gravity to that of the desired water/organic solvent ratio. The level gauge (LG) can confirm whether the concentration has reached the target concentration rate or not.

Figure 8:
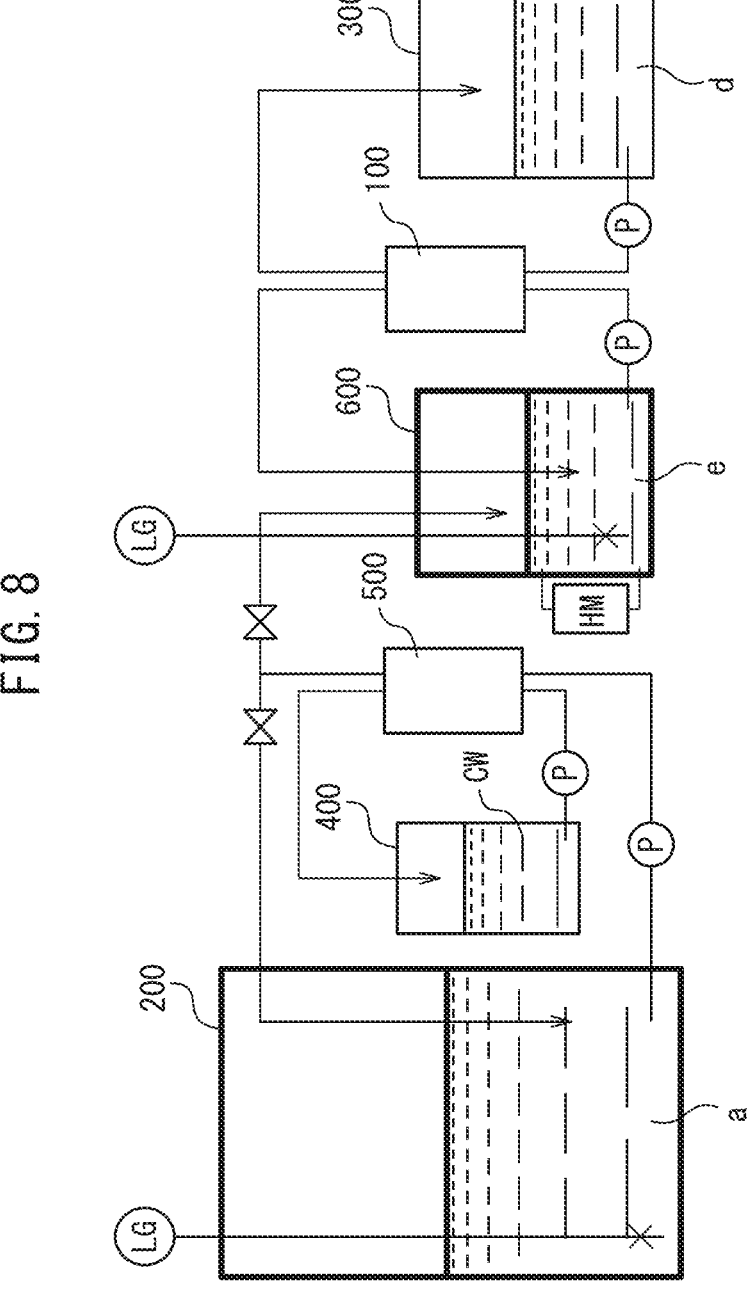
FIG. 8 is a schematic diagram for describing yet another example of the concentration system for a feed solution of the present invention.

The concentration system of FIG. 8 is yet another embodiment in which a membrane distillation method is applied as a second concentrating means, and is a system in which the first concentrating means is arranged after the second concentrating means.

In the concentration system of FIG. 8, the feed solution (a) is first sent to the membrane module (500) for membrane distillation and is concentrated by the membrane distillation method. The feed solution (a) after concentration is delivered to a product tank (600). The feed solution (a) after concentration is then sent from the product tank (600) to the forward osmotic membrane module (100), concentrated by the forward osmosis method, and thereafter returned to the product tank (600) to be circulated.

The concentration by each of the membrane module (500) for membrane distillation and the forward osmotic membrane module (100) in the concentration system of FIG. 8 is similar to that shown in the concentration system of FIG. 7. However, the feed solution (a) passes through the membrane module (500) for membrane distillation only once and is circulated in the forward osmotic membrane module (100), which differs from the system of FIG. 7.

In the concentration by the membrane distillation method, when passing through the membrane module (500) for membrane distillation only once is not sufficient for concentration, a portion of the feed solution (a) from the membrane module (500) for membrane distillation may be sent to the product tank (600), with the remaining portion returned to the feed solution tank (200) to be circulation and concentrated.

In any of the systems of FIGS. 5 to 8, taking out the feed solution (a) from the bottom portion of the tank and returning it to the bottom portion of the tank are effective in preventing loss of the solute in the feed solution (a) adhering to the tank wall surface. It is also effective to provide the inner portion of the tank with a stirring function for stable concentration.

In the systems of FIGS. 5 to 8, the specific gravity of the feed solution (a) can be tracked with a hydrometer (HM). Thus, the ratio of water and the organic solvent in the solvent of the feed solution (a) can be monitored. It is possible to carry out concentration while bringing the ratio of water and the organic solvent in the solvent (b) closer to the target value by suspending or slowing the operation of each concentration method as needed.

Finally, the volume of the feed solution (a) can be measured with a level gauge (LG), and concentration can be completed when the target concentration rate is reached.

In addition to the exemplified specific gravity, pH and conductivity as items for monitoring the characteristics of the feed solution (a) can be used. By monitoring these and the measured value of the level gauge, the weight of the solution, etc. simultaneously, concentration can be carried out while regulating the ratio of the organic solvent and water in the solvent (b) of the feed solution (a).

It has been considered that a solute component in the feed solution precipitates during the process of concentrating the feed solution. In this case, there is a risk that the precipitate may obstruct the forward osmotic membrane, the membrane for membrane distillation, the piping system, etc. and hinder the concentration. In order to avoid such circumstances, it is preferable that when at least one of the first concentration method and the second concentration method is carried out, a solid-liquid separation step of filtering the feed solution with a filter be carried out and only a liquid be supplied to the forward osmotic membrane module and the membrane module for membrane distillation.

The filter can be arranged at any site, for example, in the feed solution tank, the outlet of the forward osmosis membrane module, the outlet of the membrane module for membrane distillation, or in the piping system.

The material of the filter is not particularly limited to, for example, paper, a resin, a glass, or an inorganic substance, and may be appropriately selected from materials that are chemically and physically stable with respect to the feed solution. The opening of the filter may be appropriately set according to the size of the precipitate. From the viewpoint of preventing clogging, for example, a filter having an opening of 1 μm or greater is preferable.

Figure 9:
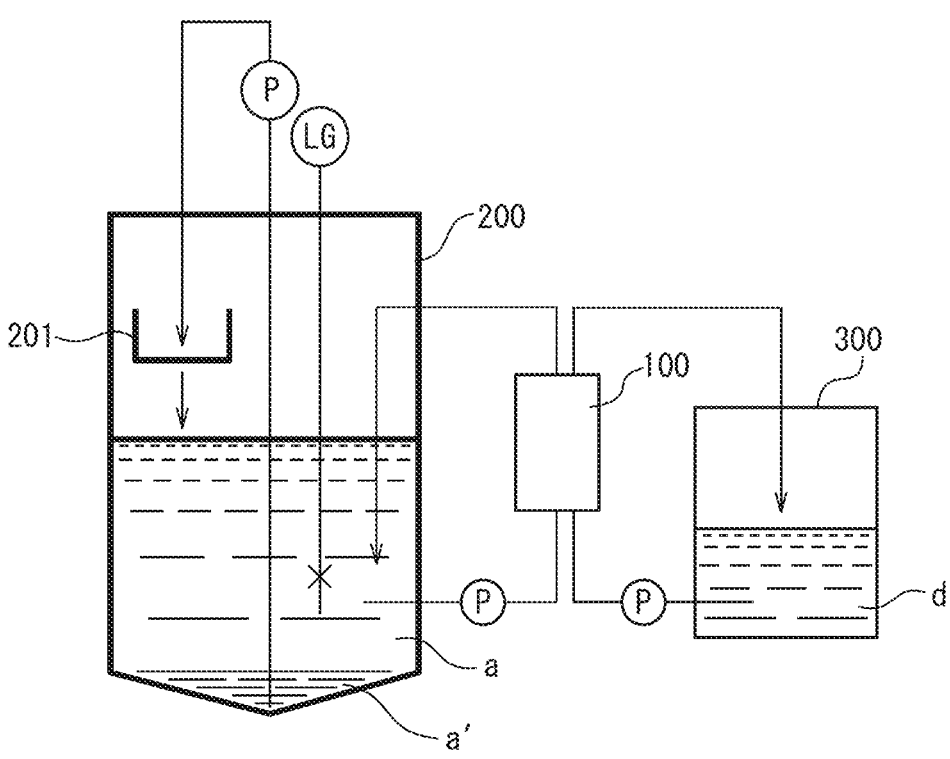
FIG. 9 is a schematic diagram for describing yet another example of the concentration system for a feed solution of the present invention.

FIG. 9 is one example of a concentration system in which the feed solution tank (200) is provided with a filter (201).

In order to show the installation of the filter (201) as a constituent element of the system in FIG. 9, only the forward osmotic membrane module (100), the feed solution tank (200), the draw solution tank (300), and the piping system in the vicinity thereof are shown with the filter (201). However, an appropriate second concentration system, such as a blower or a membrane module for membrane distillation, can be connected thereto to obtain the concentration system of the present invention.

The concentration system of FIG. 9 is configured such that the feed solution tank (200) in which the feed solution (a) is stored and concentrated comprises that filter (201) and a feed solution filtration pipe, the filter (201) is mounted higher than the liquid surface of the feed solution (a), the feed solution filtration pipe comprises an inlet at a bottom portion of the feed solution tank (200) and an outlet at an upper portion of the filter, and the feed solution (a) is delivered from the bottom portion of the feed solution tank (200) to the upper portion of the filter (201) via the feed solution filtration pipe, passes through the filter (201), and flows into the feed solution (a) in the feed solution tank (200).

With such a configuration, when a precipitate (a') precipitates from the feed solution (a), the precipitate (a') is removed from the feed solution (a) by the filter (201), and thus it is possible for only the liquid portion of the feed solution (a) to be supplied to the first or second concentrating unit for concentration to be carried out while solid-liquid separation is carried out.

The flow rate for delivering the feed solution (a) is not particularly limited, but it is preferable that the flow rate be equal to or less than the supply flow rate of the feed solution in the forward osmotic membrane treatment used in the first concentration method.

Figure 10:
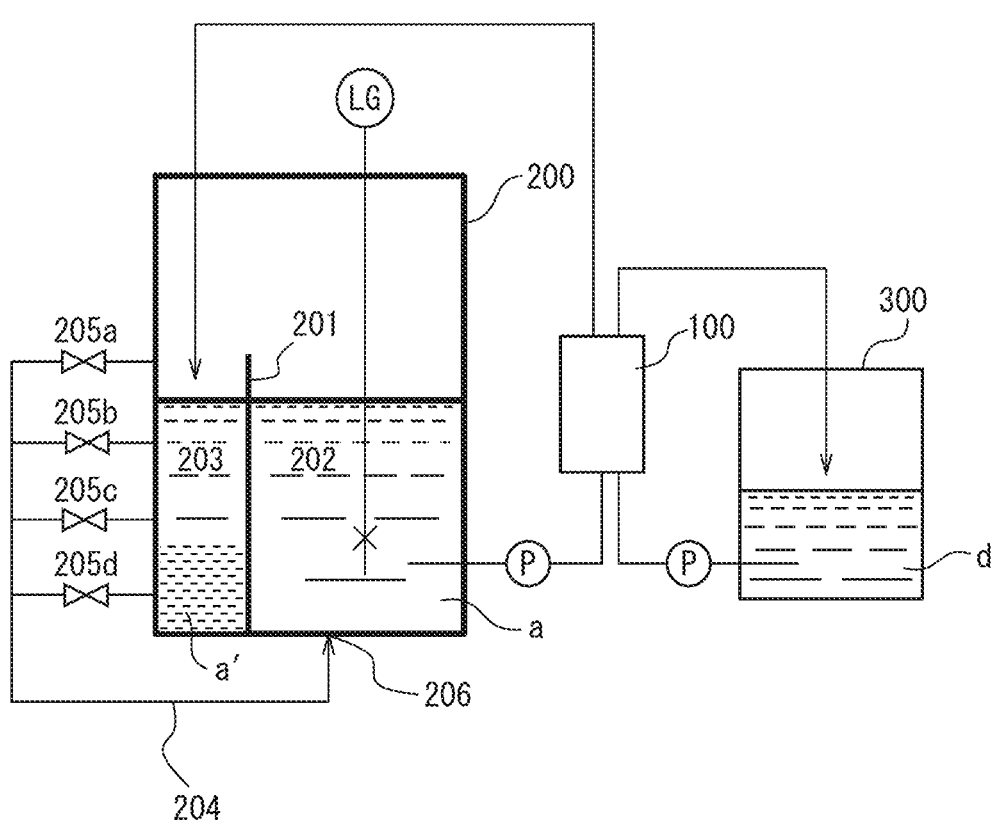
FIG. 10 is a schematic diagram for describing yet another example of the concentration system for a feed solution of the present invention.

FIG. 10 is one example of a concentration apparatus in which the feed solution tank (200) is provided therein with a partition plate (201) and the inner portion of the feed solution tank (200) is divided into a first chamber (202) and a second chamber (203) by the partition plate (201).

In order to show the installation of the partition plate (201), the first chamber (202), and the second chamber (203) as constituent elements of the system in FIG. 10, only the forward osmotic membrane module (100), the feed solution tank (200), the draw solution tank (300), and the piping system in the vicinity thereof are shown with the filter (201). However, an appropriate second concentration system, such as a blower or a membrane module for membrane distillation, can be connected thereto to obtain the concentration system of the present invention.

The concentration system of FIG. 10 is configured such that an inner portion of the feed solution tank (200) is divided into the first chamber (202) and the second chamber (203) by the partition plate (201), the system comprises a means of extracting the feed solution (a) from a bottom portion of the first chamber (202) to supply the forward osmotic membrane module (100), which is a first concentrating unit;

a means of returning a concentrated feed solution (a) obtained from the forward osmotic membrane module (100) to the second chamber (203); and a first chamber-second chamber connecting pipe (204) connecting the first chamber (202) and the second chamber (203), the first chamber-second chamber connecting pipe (204) comprises a plurality of valves (205a, 205b, 205c, 205d) connected at different heights in the second chamber (203); and an outlet (206) opening into a bottom portion of the first chamber, and the feed solution (a) in the second chamber is collected from at least one of the plurality of inlets (205a, 205b, 205c, 205d), passes through the first chamber-second chamber connecting pipe (204), and discharges from the outlet (206) to return into the first chamber (202).

The feed solution (a) extracted from the bottom portion of the first chamber (202) of the feed solution tank (200) is supplied to the forward osmotic membrane module (100), which is the first concentrating unit, as illustrated in FIG. 10. However, the feed solution (a) extracted from the bottom portion of the first chamber (202) may be supplied to an appropriate second concentrating unit, in place of the first concentrating unit or along with the first concentrating unit.

In the concentration system of FIG. 10, when the concentrated feed solution (a) contains a precipitate (a'), the precipitate (a') settles at the bottom portion of the second chamber (203) due to the difference in specific gravity from the feed solution (a), and the portion near the liquid surface of the feed solution (a) in the second chamber (203) becomes a supernatant. Only the supernatant portion of the feed solution (a) is collected from one or more valves (in FIG. 10, the second valve (204b) from the top), among the plurality of valves (205a, 205b, 205c, 205d), that are lower than the liquid surface and open to the supernatant portion, passed through the first chamber-second chamber connecting pipe (204), discharged from the outlet (206), and returned to the first chamber (202). The feed solution (a) from which the precipitate was removed can then be extracted from the bottom portion of the first chamber (202) and supplied to the first concentrating unit and/or the second concentrating unit for concentration to be carried out.

<<Feed Solution>>

The feed solution to be concentrated in the concentration method of the present invention is not particularly limited as long as the solution or the dispersion contains a solute and a solvent, and any solute and solution may be used. According to the forward osmotic membrane method and the membrane distillation method, both are capable of concentrating without heating to, for example, 50° C. or higher, and are effectively applied to a feed solution where concentrating without heating is desirable.

Examples of the applicable feed solution include foods, pharmaceuticals, seawater, and accompanying water discharged from gas fields and oil fields. Considering the advantage that concentrating without heating is possible, it is effective to apply the present invention to solutions or dispersions containing valuable substances that may be decomposed by heating, particularly drug feeds, drug substances, and drug intermediates (hereinafter, referred to as "pharmaceutical feed, etc."), as solutes.

As the pharmaceutical feed, etc., a useful substance selected from the group consisting of an amino acid, a peptide, a protein, a saccharide, a vaccine, a nucleic acid, an antibiotic, an antibody-drug conjugate (ADC), and a vitamin is used as a solute. It is preferable that the solute be dissolved or diffused in a suitable solvent.

The amino acid is a compound having one amino acid skeleton composed of a carboxyl group, an amino group, and a moiety connecting therebetween. The amino acid herein refers to a concept that encompasses essential amino acids, non-essential amino acids, and non-natural amino acids.

Examples of the essential amino acid include tryptophan, lysine, methionine, phenylalanine, threonine, valine, leucine, and isoleucine. Examples of the non-essential amino acid include arginine, glycine, alanine, serine, tyrosine, cysteine, asparagine, glutamine, proline, aspartic acid, and glutamic acid.

A non-natural amino acid refers to any artificial compound which has one amino acid skeleton in the molecule and does not exist in nature. However, examples of the non-natural amino acid as a solute of the pharmaceutical feed, etc. include ones obtained by a desired labeled compound to an amino acid skeleton. Examples of the labeled compound include dyes, fluorescent substances, luminescent substances, enzyme substrates, coenzymes, antigenic substances, and protein-binding substances.

Preferable examples of the non-natural amino acid as a solute of the pharmaceutical feed, etc. include labeled amino acids and functionalized amino acids.

The labeled amino acid is a non-natural amino acid in which an amino acid skeleton and a labeled compound are bound. Specific examples thereof include an amino acid in which a labeled compound is bound to an amino acid skeleton including an aromatic ring in a side chain.

Examples of the functionalized amino acid include photoresponsive amino acids, photoswitch amino acids, fluorescent probe amino acids, and fluorescent labeled amino acids.

A peptide refers to a compound having 2 to less than 70 amino acid residues bound together, and may be linear or cyclic. Examples of a peptide to be concentrated include L-alanyl-L-glutamine, B-alanyl-L-histidine, cyclosporine, and glutathione.

A protein generally refers to a compound having a longer chain than a peptide, among compounds having amino acid residues bound together. The protein herein is preferably one applicable as a protein formulation.

Examples of the protein formulation include interferon α, interferon β, interleukins 1 to 12, growth hormone, erythropoietin, insulin, granulocyte colony-stimulating factor (G-CSF), tissue plasminogen activator (TPA), natriuretic peptide, blood coagulation factor VIII, somatomedin, glucagon, growth hormone-releasing factor, serum albumin, and calcitonin.

Examples of the saccharide include monosaccharides, disaccharides, saccharide chains (excluding disaccharides), and saccharide chain derivatives.

Examples of the monosaccharide include glycose, fructose, galactose, mannose, ribose, and deoxyribose. Examples of the disaccharide include maltose, sucrose, and lactose.

The saccharide chain herein refers to a concept that excludes disaccharides, and examples thereof include glucose, galactose, mannose, fucose, xylose, glucuronic acid, and iduronic acid. Examples of the saccharide chain derivative include saccharide derivatives such as N-acetylglucosamine, N-acetylgalactosamine, and N-acetylneraminic acid.

Examples of the vaccine include hepatitis A vaccine, hepatitis B vaccine, and hepatitis C vaccine;

examples of the nucleic acid include an oligonucleotide, RNA, an aptamer, and a decoy; and examples of the antibiotic include streptomycin and vancomycin.

Examples of the vitamin include vitamin A, vitamin B, and vitamin C, and also include derivatives and salts thereof. Vitamin B encompasses, for example, vitamin B6 and vitamin B12.

The number-average molecular weight of the solute contained in the feed solution may be about 100 to 50,000, preferably about 100 to 30,000, more preferably about 100 to 10,000, and particularly preferably 100 to 6,000.

When the molecular weight of the solute is excessively small, the solute may permeate through the forward osmotic membrane and the semi-permeable membrane during membrane distillation. When the molecular weight is excessively large, solute adhesion to a membrane surface may occur. Neither thereof is preferable.

When the molecular weight is comparatively small (for example, a molecular weight of 500 or less), the number-average molecular weight of the solute can be obtained by calculation from the chemical formula of the solute. When the molecular weight of the solute is comparatively large (for example, a molecular weight of 500 or greater), the number-average molecular weight can be obtained as a number-average molecular weight of a polyethylene glycol equivalent measured by GPC.

The solvent of the feed solution is a liquid, and can be any inorganic solvent or organic solvent as long as the solute in the feed solution can be dissolved or diffused.

In the present invention, there is an advantage that a feed solution containing both water and an organic solvent as a solvent can be concentrated while maintaining the solvent composition. Thus, the solvent of the feed solution of the present invention contains both water and an organic solvent. The organic solvent is preferably a solvent that is compatible with water, and may be, for example, an alcohol, a ketone, or an aprotic solvent.

The solvent of the feed solution in the present invention is preferably a mixture of water and one or more selected from acetonitrile, isopropanol, acetone, methanol, and ethanol.

In the system of the present invention, the feed solution after concentration is subjected to specific gravity measurement, pH measurement, conductivity measurement, liquid level measurement, optical rotation measurement, near-infrared spectroscopic analysis, or weight measurement by online measurement. Using the measured value as a guide, concentration can be carried out while estimating and adjusting the solute concentration and the solvent composition.

When the solute contained in the feed solution is an optical rotation substance, the solute concentration can be found during the concentrating operation by the online measurement of the angle of optical rotation.

When near-infrared spectroscopic analysis is carried out online, information such as a solute concentration and a solvent composition can be found during the concentrating operation.

Examples of the online measurement used for finding the solute concentration include specific gravity measurement, conductivity measurement, liquid level measurement, optical rotation measurement, and weight measurement.

Examples of the online measurement used for finding the solvent concentration include specific gravity measurement, pH measurement, conductivity measurement, liquid level measurement, near-infrared spectroscopic analysis, and weight measurement.

Each of these online measurements can be carried out using a well-known measurement means.

The concentration system of the present invention has a measuring means for measuring online at least one of the solute concentration and the solvent composition, preferably both thereof, and can adjust the solvent composition in accordance with a value measured by the measuring means.

As a method of adjusting the solvent composition according to the measured value of the online measurement, for example, the deviation of the online measurement values from the target solute concentration and solvent composition is calculated; the operation, change in concentrating rate, or suspension of each of the first concentrating means and the second concentrating means is determined in accordance with the deviation; and adjustment is made to bring the solute concentration and solvent composition closer to the target solute concentration and solvent composition. Examples of the method of changing the concentrating rate include changing the concentrating temperature and changing the supply rate of the feed solution to each module.

The component analysis of the final concentrated product (e) may be appropriately selected in accordance with the feed solution and the solute contained in the concentrate thereof.

Well-known analysis methods, for example, ICP-MS (inductively coupled plasma mass spectrometry), nuclear magnetic resonance (NMR) method, gas chromatography-mass spectrometry (GC/MS) method, colorimetry method, fluorescence method, or high-performance liquid chromatography (HPLC) can be used.

<<Concentration Apparatus>>

According to another viewpoint of the present invention, a concentration apparatus for a feed solution is provided.

The concentration apparatus of the present invention may be any of the following:

A concentration apparatus for concentrating a feed solution containing a solute and a solvent to obtain a concentrate of the feed solution, wherein a feed solution tank for storing the feed solution is connected to
      a first concentrating unit for concentrating the feed solution by a forward osmosis method, and
      a second concentrating unit for concentrating the feed solution by removing water and an organic solvent in the feed solution through evaporation; or
  a concentration apparatus for concentrating a feed solution containing a solute and a solvent to obtain a concentrate of the feed solution, wherein
   a feed solution tank for storing the feed solution is connected to
      a first concentrating unit for concentrating the feed solution by a forward osmosis method, and
      a second concentrating unit for concentrating the feed solution by a membrane distillation method.

In any of the above cases, it is preferable that the solvent composition of the feed solution in the feed solution tank be measured online and the operation or suspension of the first concentrating unit and the second concentrating unit be automatically determined in accordance with the measured solvent composition.

Among the features described regarding the concentration system for a feed solution of the present invention, a feature applicable to a concentration apparatus can be applied to the concentration apparatus of the present invention without limitation.

<<Concentration Method>>

According to another viewpoint of the present invention, a concentration method for a feed solution is provided.

A concentration method for a feed solution, comprising concentrating a feed solution containing a solute and a solvent to obtain a concentrate of the feed solution, wherein the solvent contains water and an organic solvent, and
  the concentration method comprises a combination of
      a first concentration method of removing water in the feed solution by a forward osmosis method, and
      a second concentration method of removing water and the organic solvent in the feed solution through evaporation.

The concentration method for a feed solution can be carried out using, for example, the concentration system for a feed solution or the concentration apparatus for a feed solution of the present invention.

Among the features described regarding the concentration system for a feed solution of the present invention, a feature applicable to a concentration method can be applied to the concentration method in the present invention without limitation.

EXAMPLES

Hereinafter, the configuration and effect of the present invention will be further described with reference to specific examples. However, the present invention is not limited to the following Examples.

<Forward Osmotic Membrane Module>

A hollow-fiber support layer module having an effective intramembrane surface area of about 0.02 m² was produced by filling a cylindrical plastic housing having a diameter of 2 cm and a length of 10 cm with 130 hollow-fiber membrane ultrafiltration membranes having an inner diameter of 0.7 mm and an outer diameter of 1.0 mm and made of polyethersulfone as the substrate membrane and fixing both end portions thereof with an adhesive.

In a 0.5 L container, 10 g of m-phenylenediamine and 0.8 g of sodium lauryl sulfate were charged, which were dissolved in 489.2 of water further added therein, to prepare 0.5 kg of a first solution to be used in interfacial polymerization.

In a separate 0.5 L container, 0.8 g of trimesic acid chloride was charged, which was dissolved in 399.2 g of n-hexane added therein, to prepare 0.4 kg of a second solution to be used in interfacial polymerization.

These solutions were passed through the above hollow-fiber support layer module so as to pass through the hollow-fiber membrane interior to facilitate interfacial polymerization on the inner surface of a hollow fiber, and an active layer was formed on the hollow-fiber support layer. Thereafter, the hollow-fiber interior was washed with pure water to prepare a forward osmotic membrane module.

<Membrane Module for Membrane Distillation>

A porous hollow-fiber membrane made of PVDF, having an inner diameter of 0.7 mm and an outer diameter of 1.3 mm, and an average pore size of 0.21 μm, a maximum pore size of 0.29 μm, and a porosity of 72% determined in accordance with ASTM-F316-86, was cut to a length of 15 cm.

The module production used a thermosetting epoxy resin as the adhesive resin to adhesively fix the hollow-fiber membrane to the housing interior by centrifugal adhesion. Subsequently, the hollow-fiber membrane was adjusted so that the length of the non-adhesively fixed portion was about 10 cm and the total membrane area of the inner surface of the hollow-fiber membrane was about 0.02 m². Three membrane modules with these specifications were produced.

FS-392B manufactured by Fluoro Technology was passed through the membrane module to a state of 3-fold concentration, applied to the outside of the hollow-fiber membrane, and dried, thereby obtaining a membrane module for membrane distillation.

Among the membrane modules for membrane distillation obtained by the above method, one module was dissected to measure the characteristics of the porous hollow-fiber membrane. The water contact angle of the porous hollow-fiber membrane was calculated by dropping 2 μL of pure water under the conditions of a temperature of 23° C. and a relative humidity of 50% and analyzing the images of angles formed between the droplets and the outer surface of the hollow-fiber membrane to determine the contact angle. The measurement was carried out 5 times to calculate a numerical average. The contact angle of the outer surface of the hollow-fiber membrane was 132°, indicating very strong hydrophobicity.

<Concentration Apparatus 1>

In Example 1, concentration was carried out with a concentration apparatus 1 having the configuration shown in FIG. 5.

1 L of the feed solution (a) was charged in a feed solution tank (200) made of stainless steel. The feed solution (a) can be supplied to the forward osmotic membrane module (100) from the bottom portion of the feed solution tank (200), and piping is assembled so that the feed solution (a) concentrated by the forward osmotic membrane module (100) is returned to the bottom portion of the feed solution tank (200). In the forward osmotic membrane module (100), mainly water of the solvent (b) in the feed solution (a) is transferred to the draw solution (d), and the feed solution (a) is concentrated.

In the feed solution tank (200), an air inlet through which air is introduced into the upper portion space of the tank by a blower (BL) and an outlet through which the solvent (b) (water and the organic solvent) vaporized by the air is discharged are provided. Subsequently, both water and the organic solvent of the solvent (b) in the feed solution (a) are removed, and the feed solution (a) is concentrated.

The air and the solvent (b) discharged from the feed solution tank (200) are sent to a trap (400), and water and the organic solvent are recovered.

A level gauge (LG) and a hydrometer (HM) are connected to the feed solution tank (200).

The feed solution tank (200) is in a closed state. However, the tank is constructed such that the pressure of the inner portion of the tank is maintained at normal pressure even when the feed solution (a) is reduced.

The piping system from the feed solution tank (200) to the forward osmotic membrane module (100) has a pump (P), a flow meter (not shown), and a valve (not shown) for regulating flow rate, and the flow rate can be appropriately controlled.

A side pipe of the forward osmotic membrane module (100) is connected to an inlet pipe and an outlet pipe so that the draw solution (d) can be continuously supplied. The draw solution (d) is stored in the draw solution tank (300) and supplied to the forward osmotic membrane module (100) through the pump (P), the flow meter (not shown), and the valve (not shown) for regulating the flow rate. An aqueous solution of 25 wt % magnesium chloride was used as the draw solution (d).

<Concentration apparatus 2>

Concentration was carried out in Examples 2 to 5 and Comparative Examples 1 and 2 with a concentration apparatus 2 having the configuration shown in FIG. 6.

1 L of the feed solution (a) was charged in a feed solution tank (200) made of stainless steel. The feed solution (a) can be supplied to each of the forward osmotic membrane module (100) and the membrane module (500) for membrane distillation from the bottom portion of the feed solution tank (200), and piping is assembled so that the feed solution (a) concentrated by each module is returned to the bottom portion of the feed solution tank (200). The feed solution tank (200) is in a closed state. However, the tank is constructed such that the pressure of the inner portion of the tank is maintained at normal pressure even when the feed solution (a) is reduced. A level gauge (LG) and a hydrometer (HM) are connected to the feed solution tank (200).

The piping from the feed solution tank (200) to the forward osmotic membrane module (100) has a pump (P), a flow meter (not shown), and a valve (not shown) for regulating flow rate, and the flow rate can be appropriately controlled.

A side pipe of the forward osmotic membrane module (100) is connected to an inlet pipe and an outlet pipe so that the draw solution (d) can be continuously supplied. The draw solution (d) is stored in the draw solution tank (300) and supplied to the forward osmotic membrane module (100) through the pump (P), the flow meter (not shown), and the valve (not shown) for regulating the flow rate. An aqueous solution of 25 wt % magnesium chloride was used as the draw solution (d).

A pump (P), a flow meter (not shown), and a valve (not shown) for regulating the flow rate are arranged in the piping from the feed solution tank (200) to the membrane module (500) for membrane distillation. The feed solution (a) is supplied to the membrane module (500) for membrane distillation through a thermostat (not shown) for regulating the feed solution to a constant temperature and a heat exchanger (not shown). The concentrated feed solution (a) is then returned to the feed solution tank (200) from the outside of the membrane module (500) for membrane distillation.

A side pipe of the membrane module (500) for membrane distillation is connected to an inlet pipe and an outlet pipe so that the cooling water (CW) can be continuously supplied. The cooling water (CW) is stored in a cooling water tank (700) and supplied to the membrane module (500) for membrane distillation through a pump (P), a flow meter (not shown), and a valve (not shown) for regulating flow rate. The cooling water (CW) is supplied to the membrane module (500) for membrane distillation through a thermostat (not shown) for regulating the cooling water (CW) to a constant temperature and a heat exchanger (not shown).

Since the solvent (b) (water and the organic solvent) is transferred from the feed solution (a) to the cooling water (CW) in the membrane module (500) for membrane distillation, the volume increases with continuous concentrating operation. Therefore, the cooling water tank (700) is provided with an overflow and has a structure in which a portion of the increased portion of the cooling water (CW) is discharged to outside of the system.

In both concentration apparatuses 1 and 2, as the solvent (b) (water and the organic solvent) is removed with the progress of concentration, the volume of the feed solution (a) in the feed solution tank (200) decreases. Thus, the progress of concentration can be found by measuring the change in liquid level with the volumetric decrease of the feed solution (a) in the feed solution tank (200).

In the Examples, an experiment was carried out such that the concentrating operation was carried out until the liquid level of the feed solution (a) in the feed solution tank (200) reached a predetermined target value.

The following control methods were followed for concentration with the concentration apparatuses 1 and 2.
(1) Down to 20%+Target Liquid Level Both the forward osmotic membrane module (100) and the blower (BL), in case of the concentration apparatus 1, or the membrane module (500) for membrane distillation, in case of the concentration apparatus 2, are operated.
(2) 20% to 0%+Target Liquid Level The specific gravity of the concentrated feed solution (a) is measured, operation is carried out according to the following criteria.
  a) When the specific gravity is appropriate: Operation of both the forward osmotic membrane module (100) and the blower (BL) (concentration apparatus 1) or the membrane module (500) for membrane distillation (concentration apparatus 2) is continued.
  b) When the specific gravity is high: This case means that the proportion of water in the solvent (b) of the concentrated feed solution (a) is excessive. Thus, operation of the blower (BL) (concentration apparatus 1) or the membrane module (500) for membrane distillation (concentration apparatus 2) is suspended, and only the operation of the forward osmotic membrane module (100) is continued.
  c) When the specific gravity is low: This case means that the proportion of the organic solvent in the solvent (b) of the concentrated feed solution (a) is excessive. Thus, operation of the forward osmotic membrane module (100) is suspended, and operation of the blower (BL) (concentration apparatus 1) or the membrane module (500) for membrane distillation (concentration apparatus 2) is continued.
(3) Below the Target Liquid Level:

The specific gravity of the concentrated feed solution (a) is measured, operation is carried out according to the following criteria.
  a) When the specific gravity is appropriate: Concentrating operation is immediately terminated.
  b) When the specific gravity is high: Operation of the blower (BL) (concentration apparatus 1) or the membrane module (500) for membrane distillation (concentration apparatus 2) is suspended, and only the operation of the forward osmotic membrane module (100) is continued. Once the appropriate specific gravity is reached, concentrating operation is terminated.
  c) When the specific gravity is low: Operation of the forward osmotic membrane module (100) is suspended, and operation of the blower (BL) (concentration apparatus 1) or the membrane module (500) for membrane distillation (concentration apparatus 2) is continued. Once the appropriate specific gravity is reached, concentrating operation is terminated.

Example 1

The concentration apparatus 1 was used in Example 1.

A solution containing 0.3 wt % of tryptophan as the solute added to a mixed solvent of 900 mL of water and 100 mL of acetonitrile was filled as a model solution of the feed solution (a) into a feed solution tank (200).

This feed solution (a) and an aqueous solution having a 25 wt % concentration of magnesium chloride as the draw solution (d) were flowed into the forward osmotic membrane module (100).

Air was continuously flowed into the upper portion space of the feed solution tank (200) at a flow rate of 10 L/min with a blower (BL).

The target concentration rate was set to 10-fold or greater, and the ratio of the acetonitrile in the solvent (b) was set to 10% by volume.

As a result of the concentrating operation for 8 hours, the concentration rate reached 10-fold or greater, and a concentrate having the ratio of the acetonitrile at 10% by volume was obtained. The temperature of the feed solution during the concentration was 27 to 30° C.

The analysis results are as follows:

When the draw solution (magnesium chloride aqueous solution) used for concentration was analyzed with a UV-2400PC (Shimadzu) UV-visible spectrophotometer, tryptophan was not detected; and the analysis of the tryptophan in the concentrated feed solution confirmed that denaturation of the tryptophan did not occur.

Thus, it was verified that the concentration of the feed solution without heating was carried out without damaging the solute in the feed solution.

Example 2

The concentration apparatus 2 was used in Example 2.

A solution containing 0.3 wt % of tryptophan as the solute added to a mixed solvent of 900 mL of water and 100 mL of acetonitrile was filled as a model solution of the feed solution (a) into a feed solution tank (200).

The feed solution (a) and an aqueous solution having a 25 wt % concentration of magnesium chloride as the draw solution (d) were flowed into the forward osmotic membrane module (100).

The feed solution (a) regulated to a temperature of 30° C. and cooling water (CW) regulated to a temperature of 10° C. were flowed into a membrane module (500) for membrane distillation, and concentration by both forward osmotic membrane method and membrane distillation method was carried out.

The target concentration rate was set to 10-fold or greater, and the ratio of the acetonitrile in the solvent (b) was set to 10% by volume.

As a result of the concentrating operation for 6 hours, the concentration rate reached 10-fold or greater, and a concentrate having the ratio of the acetonitrile in the solvent (b) at 10% by volume was obtained. The temperature of the feed solution during the concentration was 29 to 33° C.

The analysis results are as follows:

When the draw solution (magnesium chloride aqueous solution) used for concentration and the cooling water were analyzed with the UV-visible spectrophotometer, tryptophan was not detected;

the analysis of the tryptophan in the concentrated feed solution confirmed that denaturation of the tryptophan did not occur; and when the concentration of the magnesium contained in the concentrated feed solution (a) was analyzed by the ICP-MS method, the transfer rate of the magnesium from the draw solution to the concentrate per membrane surface area of 1 $m^2$ per hour was merely 0.14 $g/m^2/hr$.

Thus, it was verified that the concentration of the feed solution without heating was carried out without damaging the solute in the feed solution, and that only a trace amount of the draw solution was mixed in the concentrate.

Example 3

The concentration apparatus 2 was used in Example 3.

A solution containing 0.6 wt % of "insulin, human, recombinant" (manufactured by FUJIFILM Wako Pure Chemical Corporation) as the solute added to a mixed solvent of 900 mL of water and 100 mL of acetonitrile was filled as a model solution of the feed solution (a) into a feed solution tank (200).

The feed solution (a) and an aqueous solution having a 25 wt % concentration of magnesium chloride as the draw solution (d) were flowed into the forward osmotic membrane module (100).

The feed solution (a) regulated to a temperature of 30° C. and cooling water (CW) regulated to a temperature of 10° C. were flowed into a membrane module (500) for membrane distillation, and concentration by both forward osmotic membrane method and membrane distillation method was carried out.

The target concentration rate was set to 10-fold or greater, and the ratio of the acetonitrile in the solvent (b) was set to 10% by volume.

As a result of the concentrating operation for 6 hours, the concentration rate reached 10-fold or greater, and a concentrate having the ratio of the acetonitrile in the solvent (b) at 10% by volume was obtained. The temperature of the feed solution during the concentration was 27 to 32° C. When the magnesium chloride solution used for concentration and the cooling water were analyzed with the UV-visible spectrophotometer, the "insulin, human, recombinant" was not detected. Thus, it was determined that the concentration was carried out.

Example 4

Except that 500 mL of water and 500 mL of acetonitrile were mixed and used as the solvent of a model solution of the feed solution (a) and the concentration target was changed as described below, the concentrating operation was carried out in the same manner as in Example 2.

The target concentration rate was set to 10-fold or greater, and the ratio of the acetonitrile in the solvent (b) was set to 50% by volume.

As a result of the concentrating operation for 6 hours, the concentration rate reached 10-fold or greater, and a concentrate having the ratio of the acetonitrile in the solvent (b) at 50% by volume was obtained. The temperature of the feed solution during the concentration was 37 to 42° C.

Example 5

The concentration apparatus 2 was used in Example 5.

A solution containing 0.3 wt % of tryptophan as the solute added to a mixed solvent of 900 mL of water and 100 mL of acetonitrile was filled as a model solution of the feed solution (a) into a feed solution tank (200).

The feed solution (a) and an aqueous solution having a 50 wt % concentration of isopropanol as the draw solution (d) were flowed into the forward osmotic membrane module (100).

The feed solution (a) regulated to a temperature of 30° C. and cooling water (CW) regulated to a temperature of 10° C. were flowed into a membrane module (500) for membrane distillation, and concentration by both forward osmotic membrane method and membrane distillation method was carried out.

The target concentration rate was set to 10-fold or greater, the ratio of the acetonitrile in the solvent (b) was set to 10% by volume, and the ratio of the isopropanol in the solvent (b) was set to less than 5% by volume.

As a result of the concentrating operation for 4 hours, the concentration rate reached 10-fold or greater, and a concentrate having the ratio of the acetonitrile in the solvent (b) at 10% by volume and the ratio of isopropanol in the solvent (b) of less than 1% by volume was obtained. The temperature of the feed solution during the concentration was 29 to 33° C.

The analysis results are as follows:

When the draw solution (isopropanol aqueous solution) used for concentration and the cooling water were analyzed with the UV-visible spectrophotometer, tryptophan was not detected; and the analysis of the tryptophan in the concentrated feed solution confirmed that denaturation of the tryptophan did not occur.

Thus, it was verified that the concentration of the feed solution without heating was carried out without damaging the solute in the feed solution.

Example 6

Except that 900 mL of water and 100 mL of isopropanol were mixed and used as the solvent of a model solution of the feed solution (a) and the concentration target was changed as described below, the concentrating operation was carried out in the same manner as in Example 2.

The target concentration rate was set to 10-fold or greater, and the ratio of the isopropanol in the solvent (b) was set to 10% by volume.

As a result of the concentrating operation for 6 hours, the concentration rate reached 10-fold or greater, and a concentrate having the ratio of the isopropanol in the solvent (b) at 10% by volume was obtained. The temperature of the feed solution during the concentration was 8 to 12° C.

Example 7

Except that the concentrating operation was initiated using only the forward osmotic membrane module (100) without using the membrane module (500) for membrane distillation and carried out in this state up to a concentration rate of 8-fold, and then the concentrating operation was continued using only the membrane module (500) for membrane distillation without using the forward osmotic membrane module (100) and carried out up to a concentrate rate of 10-fold, the concentrating operation was carried out in the same manner as in Example 2.

The time required to concentrate the feed solution (a) up to 8-fold with the forward osmotic membrane module was 9 hours, and the time required to concentrate up to 10-fold with the membrane module for membrane distillation was 1 hour (for a total of 10 hours). It is considered that concentrating by the forward osmotic membrane module took time because the acetonitrile concentration in the solvent increased during concentration, and the rate of forward osmosis treatment by the forward osmotic membrane module slowed down.

In the feed solution (a) at the time of 8-fold concentration, the ratio of the acetonitrile in the solvent was 21% by volume, which significantly changed from the starting composition. However, in the feed solution (a) after 10-fold concentration, the ratio of the acetonitrile in the solvent (b) was 15% by volume. Thus, it was possible to concentrate to the same solvent composition as that at starting.

When the concentration of magnesium contained in the feed solution (a) after 10-fold concentration was measured by the ICP-MS method, the transfer rate of the magnesium from the draw solution to the concentrate, per membrane area of 1 m$^2$ per hour, was 2.2 g/m$^2$/hr.

Example 8

Except that the concentrating operation was initiated using only the membrane module (500) for membrane distillation without using the forward osmotic membrane module (100) and carried out in this state up to a concentration rate of 8-fold, and then the concentrating operation was continued using only the forward osmotic membrane module (100) without using the membrane module (500) for membrane distillation and carried out up to a concentrate rate of 10-fold, the concentrating operation was carried out in the same manner as in Example 2.

When the feed solution (a) was concentrated 1.2-fold, cloudiness occurred in a portion of the feed solution (a). It is submitted that tryptophan precipitated.

In the feed solution (a) at this time, the ratio of the acetonitrile in the solvent (b) was reduced to 3.6% by volume.

The total time required to concentrate the feed solution (a) 10-fold was 7 hours.

In the feed solution (a) after 10-fold concentration, the ratio of the acetonitrile in the solvent was 7.7% by volume. The ratio of the acetonitrile in the solvent was lower than that at starting.

When the concentration of magnesium contained in the feed solution (a) after 10-fold concentration was measured by the ICP-MS method, the transfer rate of the magnesium from the draw solution to the concentrate, per membrane area of 1 m$^2$ per hour, was 0.16 g/m$^2$/hr. It was verified that only a trace amount of the draw solution was mixed in the concentrate.

Comparative Example 1

Except that the membrane module (500) for membrane distillation was not used and only the forward osmotic membrane module (100) was used, the concentrating operation was carried out in the same manner as in the Examples.

For the feed solution (a) concentrated to 10-fold by the forward osmotic membrane module (100) only, the ratio of the acetonitrile in the solvent (b) increased to 35% by volume, and a concentrate having the target composition could not be obtained. The temperature of the feed solution during the concentration was 25 to 27° C.

When the concentration of magnesium contained in the concentration was measured by the ICP-MS method, the transfer rate of the magnesium from the draw solution to the concentrate, per membrane area of 1 m$^2$ per hour, was 3.5 g/hr/m$^2$, which is greater than that of Example 2. The assumed reason for this is that the ratio of the acetonitrile in the solvent of the feed solution (a) increased during concentration, causing a structural change, such as swelling, in the forward osmotic membrane.

Comparative Example 2

Except that the forward osmotic membrane module (100) was not used and only the membrane module (500) for membrane distillation was used, the concentrating operation was carried out in the same manner as in the Examples.

According to the membrane module (500) for membrane distillation only, the ratio of the acetonitrile in the solvent (b) was less than 1% by volume at the stage in which the concentration rate was less than 10-fold, and the concentration was not able to reach the target rate. The temperature of the feed solution during concentration was 26 to 30° C.

REFERENCE SIGNS LIST

100 forward osmotic membrane module
110, 210 housing
111 draw solution inlet
112 draw solution outlet
120 forward osmotic membrane
121 substrate layer
122 active layer 130, 230 adhesive resin
200 feed solution tank
201 partition plate
202 first chamber
203 second chamber
204 first chamber-second chamber connecting pipe
205*a*, 205*b*, 205*c*, 205*d* valve
206 outlet
211 cooling water inlet
212 cooling water outlet
220 membrane for membrane distillation
300 draw solution tank
400 trap
500 membrane module for membrane distillation
600 product tank
700 cooling water tank
a feed solution
a' precipitate
b solvent
c concentrate
d draw solution
e concentrated product
BL blower
CW cooling water
HM hydrometer
LG level gauge
P pump

The invention claimed is:

1. A concentration method for a feed solution containing a solute and a solvent to obtain a concentrate of the feed solution, wherein the solvent contains water and an organic solvent, and
the concentration method comprises a combination of
    a first concentration method of removing water in the feed solution by a forward osmosis method, and
    a second concentration method of removing water and the organic solvent in the feed solution through evaporation, wherein the first concentration method and the second concentration method are carried out in parallel.

2. The concentration method for a feed solution according to claim 1, wherein the concentration method of removing water and the organic solvent in the feed solution through evaporation is a membrane distillation method.

3. The concentration method for a feed solution according to claim 1, wherein at least one of a solute concentration and a solvent composition in the concentrate of the feed solution is measured online, and execution, change in concentrating rate, or suspension of the first concentration method and the second concentration method is determined in accordance with the measured value.

4. The concentration method for a feed solution according to claim 3, wherein at least one of the solute concentration and the solvent composition in the concentrate of the feed solution is measured by one or more measuring means selected from the group consisting of specific gravity measurement, pH measurement, conductivity measurement, liquid level measurement, optical rotation measurement, near-infrared spectroscopic analysis, and weight measurement of the concentrate.

5. The concentration method for a feed solution according to claim 1, wherein the solvent is a mixture containing water and
    one or more selected from the group consisting of acetonitrile, methanol, ethanol, and isopropanol.

6. The concentration method for a feed solution according to claim 1, wherein the solute is one or more selected from the group consisting of an amino acid, a peptide, a protein, a saccharide, a vaccine, a nucleic acid, an antibiotic, an antibody-drug conjugate (ADC), and a vitamin.

7. The concentration method for a feed solution according to claim 1, wherein the solute has a number-average molecular weight of 100 to 50,000.

8. The concentration method for a feed solution according to claim 1, wherein the temperature of the feed solution is regulated to a range of 1° C. to 50° C.

9. The concentration method for a feed solution according to claim 1, wherein an alcohol selected from methanol, ethanol, isopropanol, and t-butanol is used as a solute of a draw solution used in the forward osmosis method.

10. The concentration method for a feed solution according to claim 1, wherein when at least one of the first concentration method and the second concentration method is carried out,
a solid-liquid separation step of filtering the feed solution is carried out.

11. A concentration method for a feed solution containing a solute and a solvent to obtain a concentrate of the feed solution, wherein the solvent contains water and an organic solvent, and
the concentration method comprises a combination of
    a first concentration method of removing water in the feed solution by a forward osmosis method, and
    a second concentration method of removing water and the organic solvent in the feed solution through evaporation, wherein the concentration method is carried out while controlling the ratio of water and the organic solvent in the solvent in the feed solution to be concentrated.

12. The concentration method for a feed solution according to claim 1, wherein the concentration method is carried out while controlling the ratio of water and the organic solvent in the solvent in the feed solution to be concentrated.

* * * * *